United States Patent
Kraus

(10) Patent No.: US 9,629,661 B2
(45) Date of Patent: Apr. 25, 2017

(54) SET OF INSTRUMENTS FOR THE PERCUTANEOUS STABILIZATION OF THE SPINE WITH THE AID OF PEDICLE SCREWS AND RODS

(71) Applicant: Kilian Kraus, Werneck (DE)

(72) Inventor: Kilian Kraus, Werneck (DE)

( * ) Notice: Subject to any disclaimer, the term of this patent is extended or adjusted under 35 U.S.C. 154(b) by 197 days.

(21) Appl. No.: 14/444,016

(22) Filed: Jul. 28, 2014

(65) Prior Publication Data

US 2016/0022317 A1   Jan. 28, 2016

(30) Foreign Application Priority Data

Jul. 26, 2014  (DE) ......................... 10 2013 108 036

(51) Int. Cl.
*A61B 17/70* (2006.01)

(52) U.S. Cl.
CPC ........ *A61B 17/7002* (2013.01); *A61B 17/708* (2013.01); *A61B 17/7074* (2013.01); *A61B 17/7083* (2013.01); *A61B 17/7091* (2013.01)

(58) Field of Classification Search
CPC ................... A61B 17/7074–17/7098
USPC ............................. 606/86 A, 86 R
See application file for complete search history.

(56) References Cited

U.S. PATENT DOCUMENTS

| | | |
|---|---|---|
| 2006/0036255 A1 | 2/2006 | Pond, Jr. et al. |
| 2009/0228053 A1 | 9/2009 | Kolb et al. |
| 2010/0249856 A1 | 9/2010 | Iott et al. |
| 2011/0313464 A1* | 12/2011 | McLean ............... A61B 17/708 606/279 |
| 2012/0022594 A1* | 1/2012 | Walker ................. A61B 17/708 606/264 |
| 2012/0031792 A1 | 2/2012 | Petit |
| 2013/0103039 A1 | 4/2013 | Hopkins et al. |

* cited by examiner

*Primary Examiner* — Nicholas Plionis
(74) *Attorney, Agent, or Firm* — Laurence A. Greenberg; Werner H. Stemer; Ralph E. Locher

(57) ABSTRACT

The invention relates to an instrument set for percutaneous stabilization of the spinal column using rods (8) and pedicle screws (1) that have a screw head (3) and a screw shank (4) and a distally open recess (13) for receiving a rod (8), with a screw manipulator (2) through which a central cavity (11) passes axially and which comprises a cylindrical sleeve (20) and a slide (24), wherein
  the wall of the cylindrical sleeve (20) is divided into two first wall segments (27) by two diametrically opposite and axially extending windows (26) which open out in the proximal end face of the sleeve (20),
  the proximal ends of the first wall segments (27) form grip elements (28) which, during a screw manipulation, receive between them at least a longitudinal portion of the screw head (3), and
  the slide (24) is displaceable in the axial direction on the sleeve (20) and is connected to the first wall segments (27) such that it secures these against moving radially apart at least in a proximal end position (E) of displacement.

41 Claims, 23 Drawing Sheets

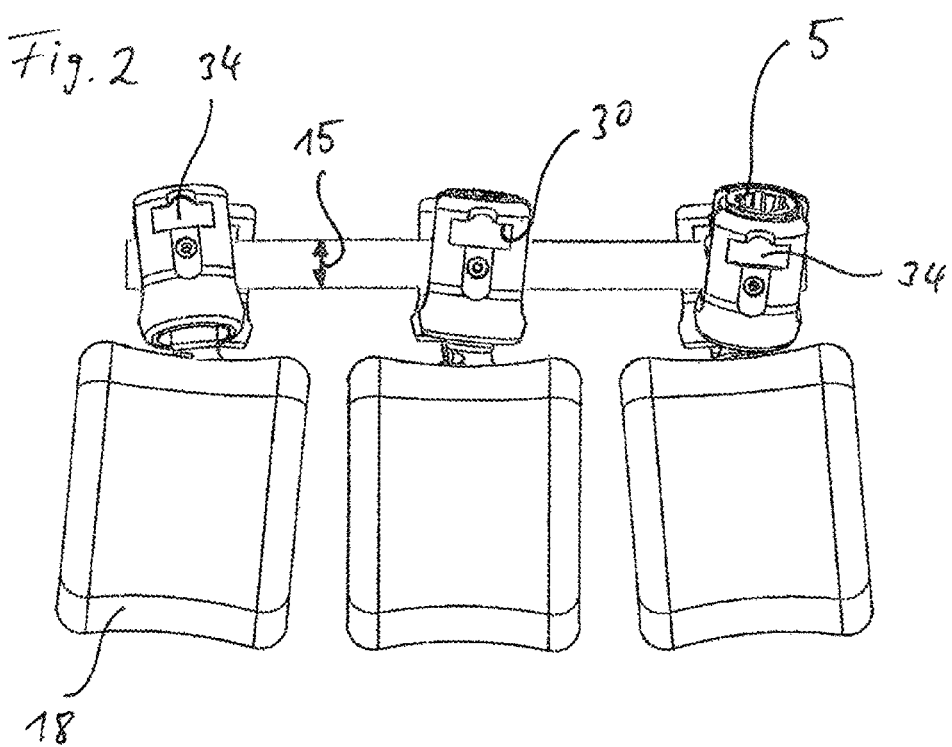

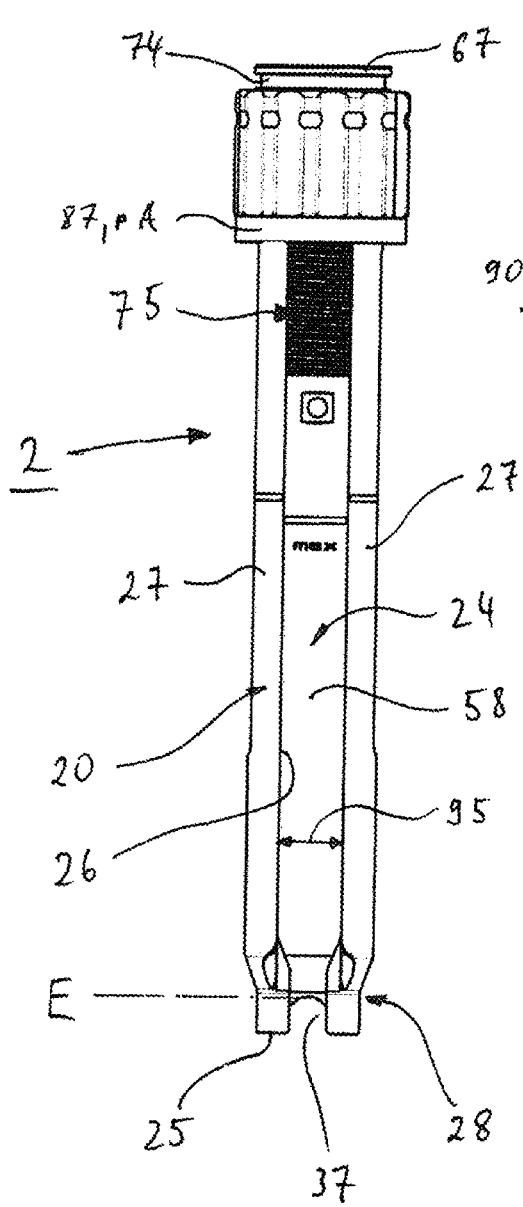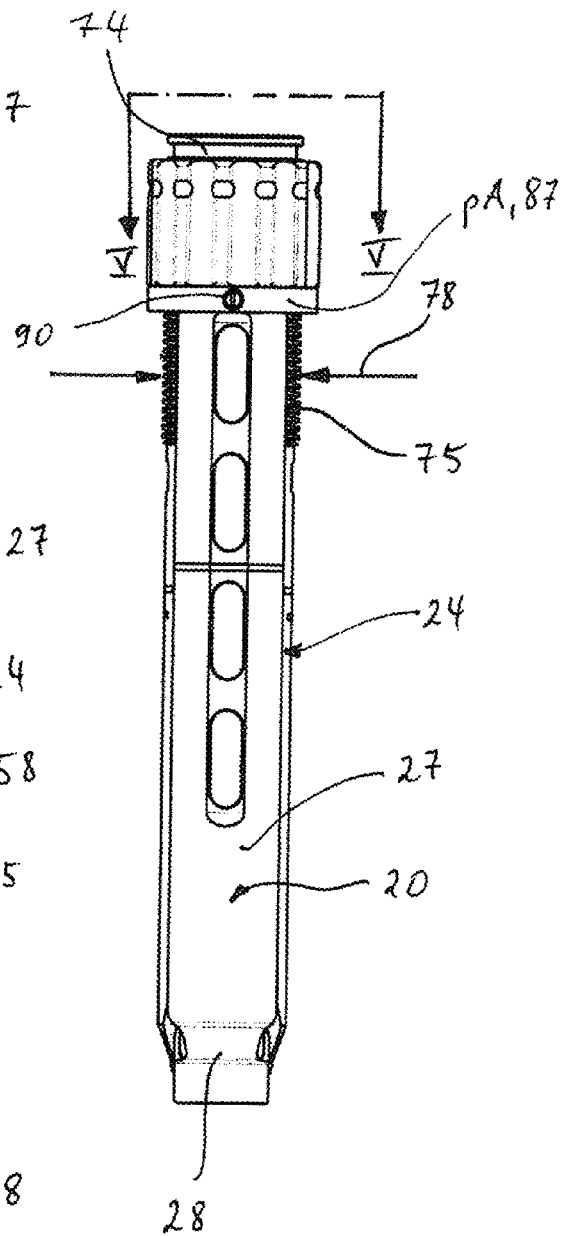

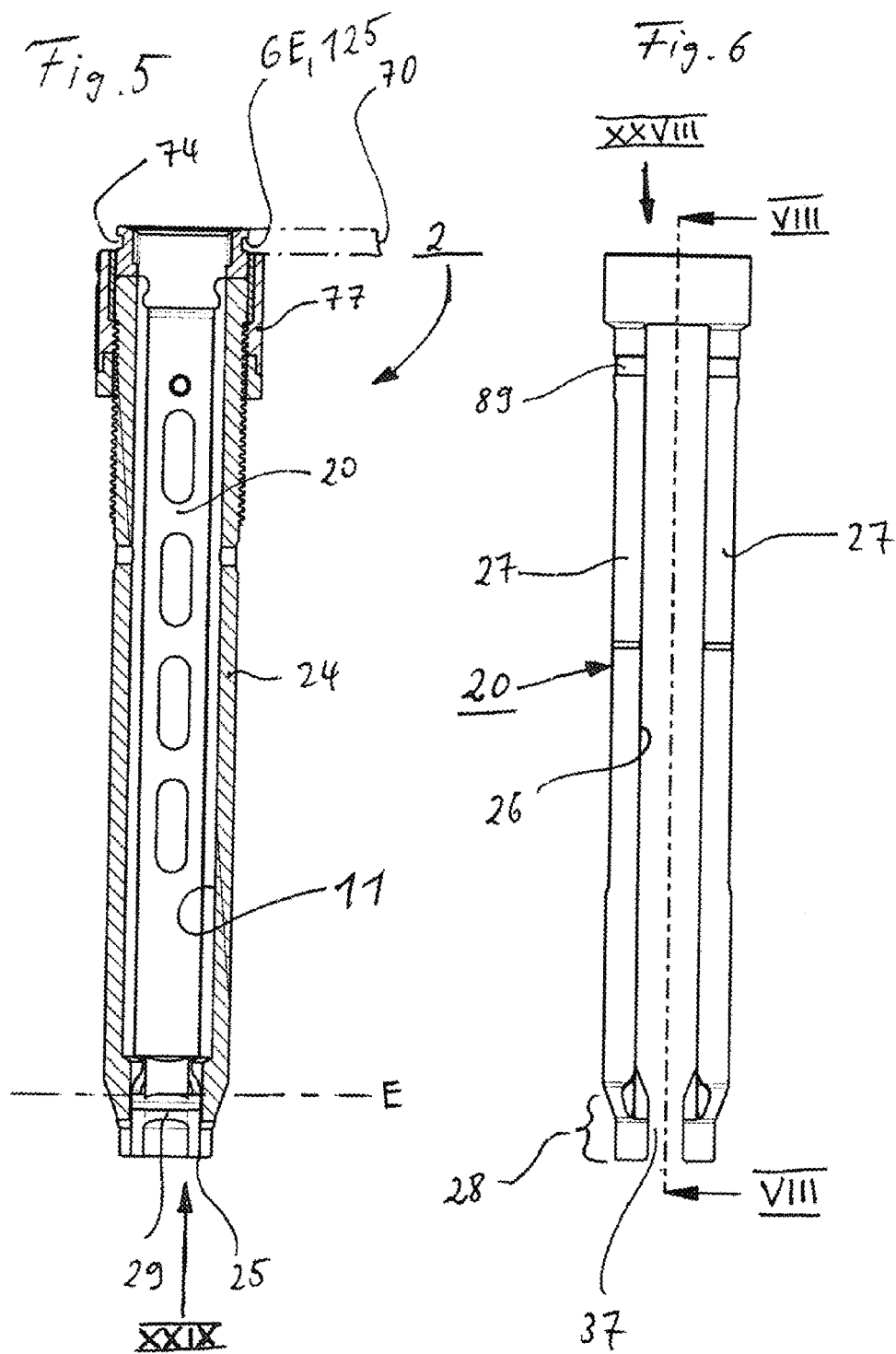

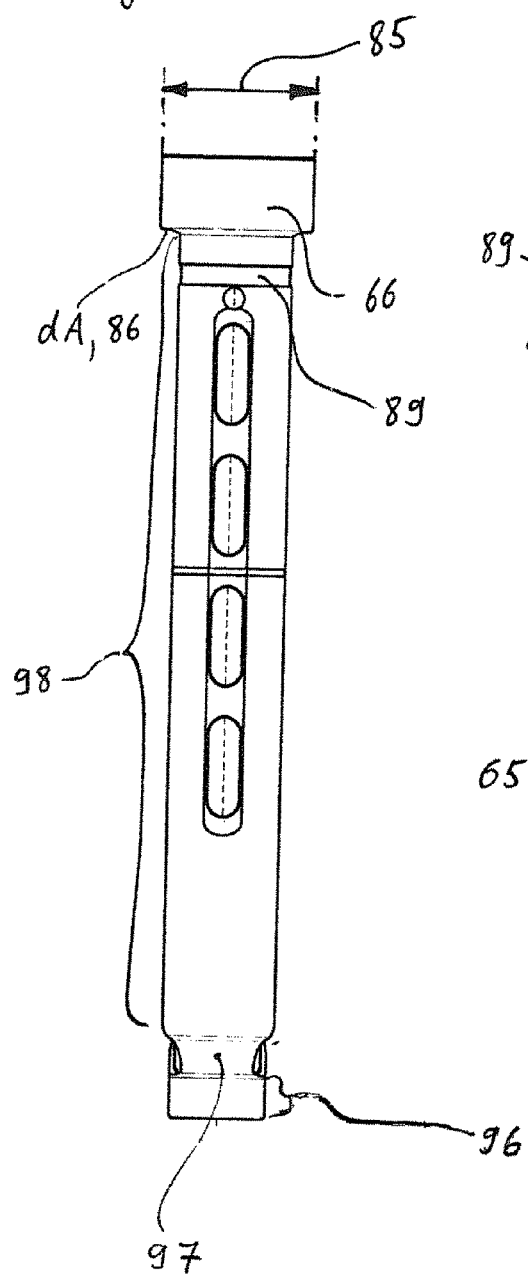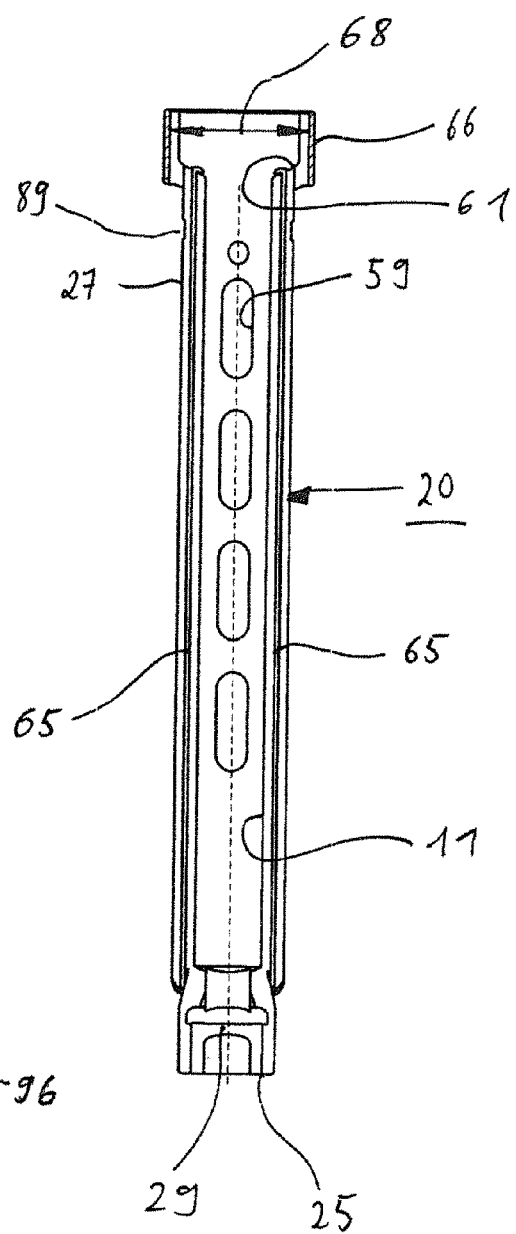

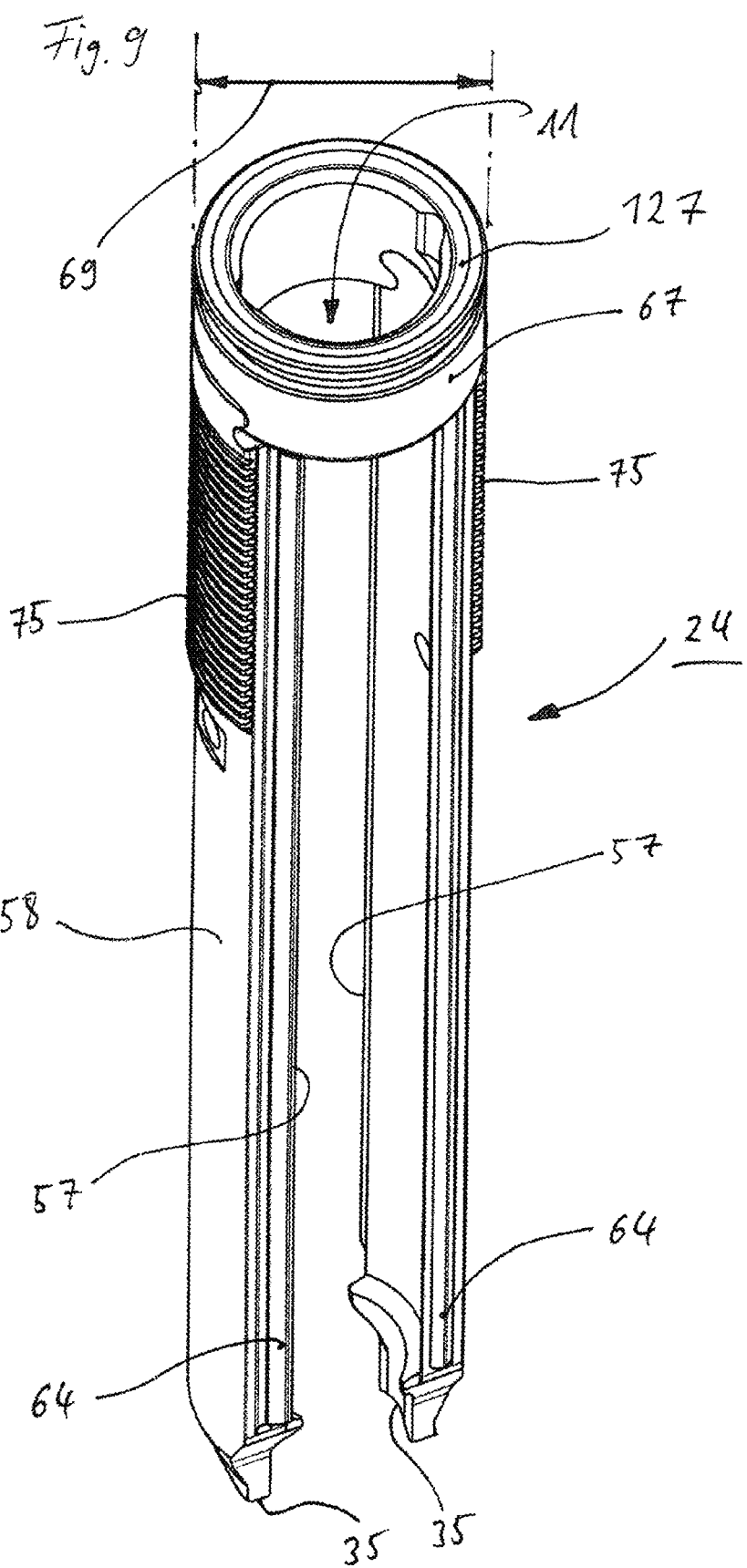

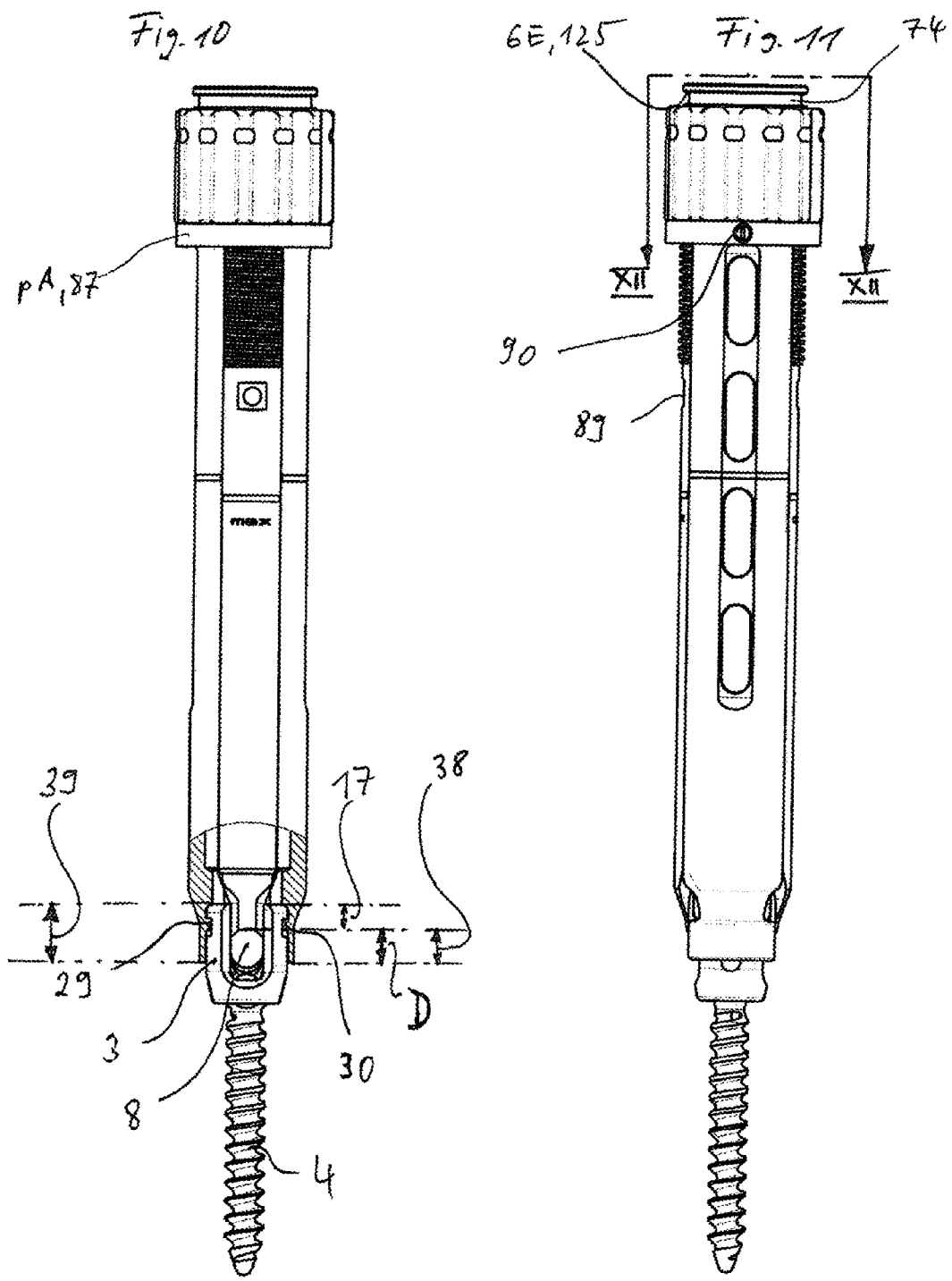

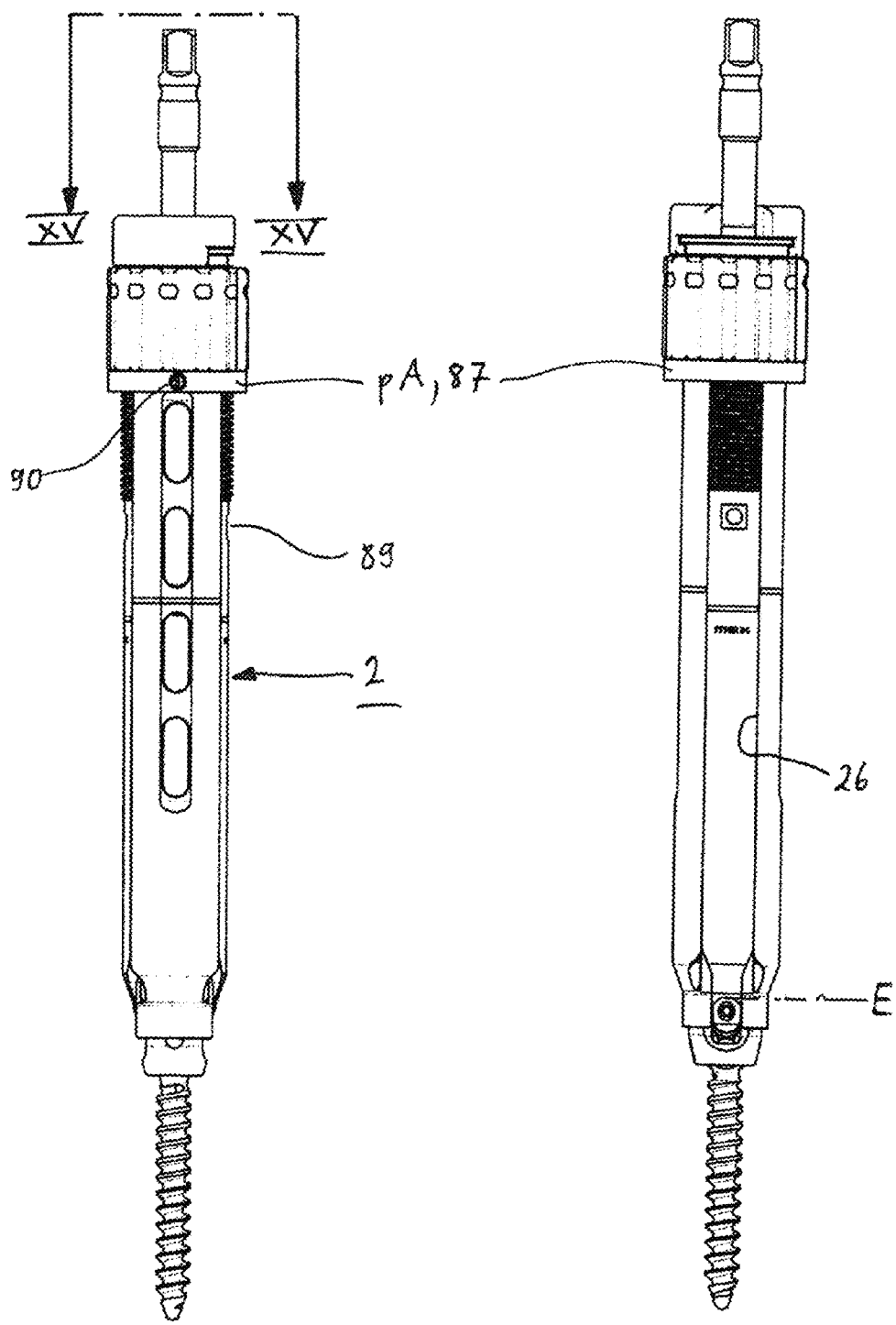

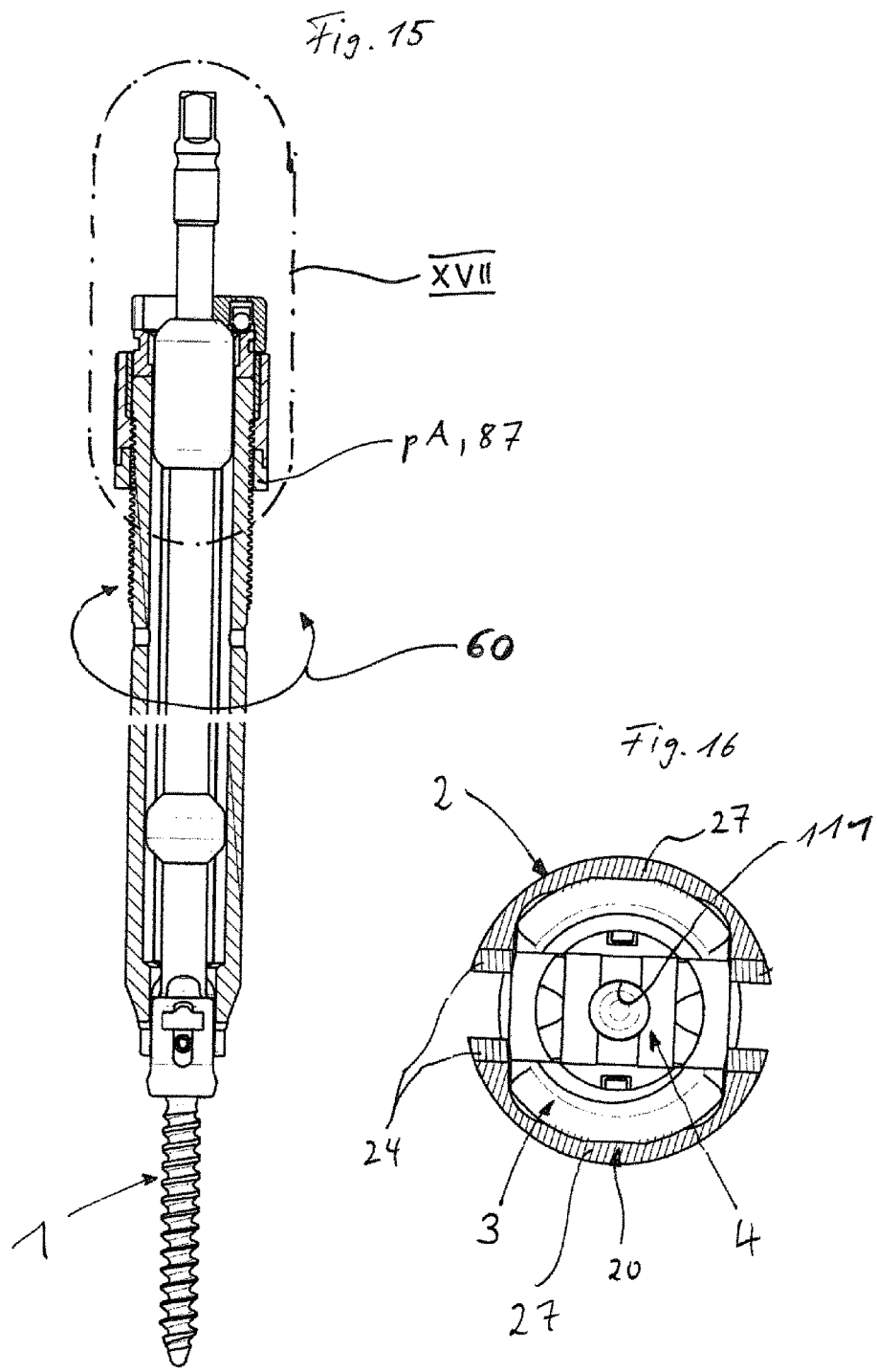

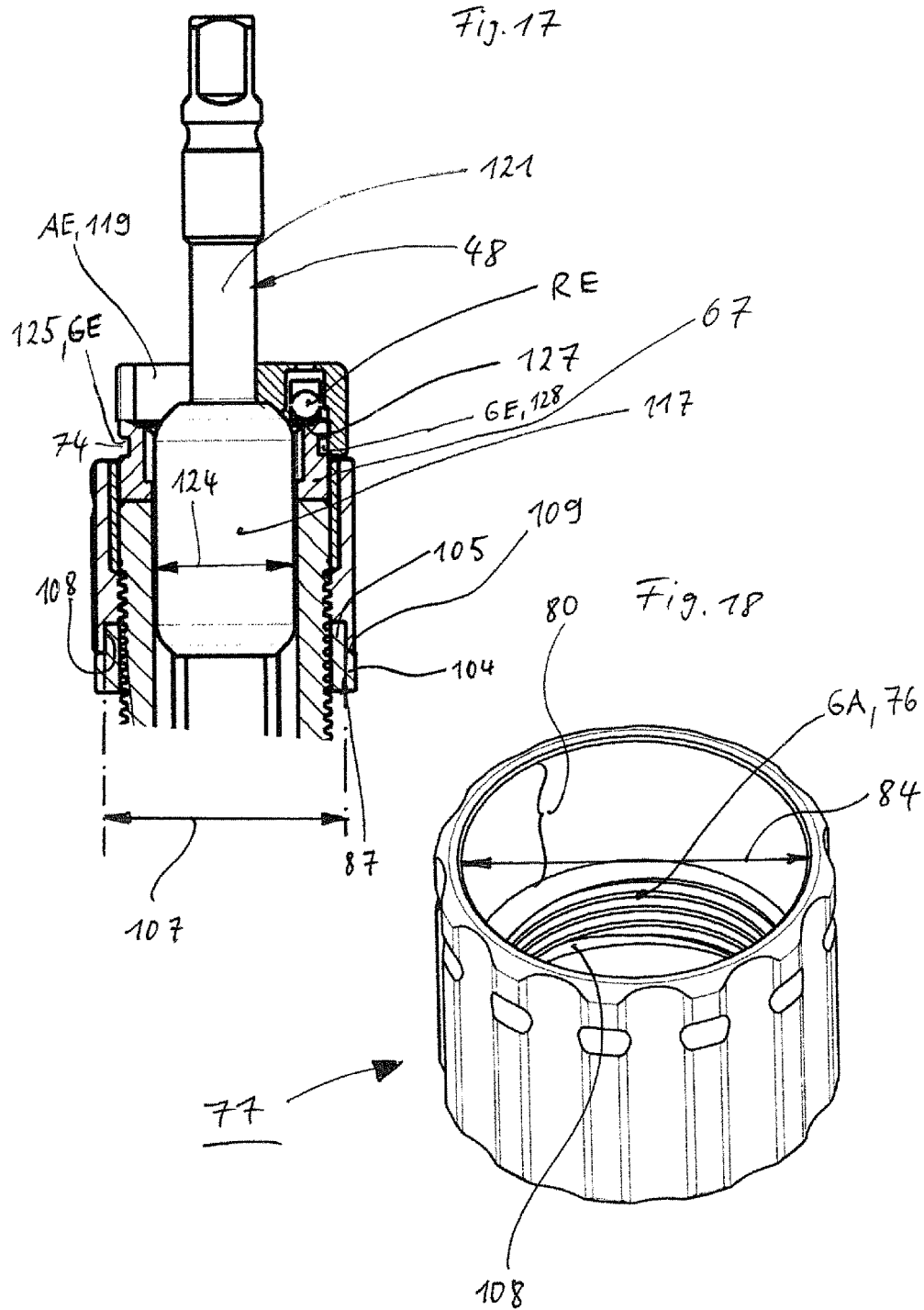

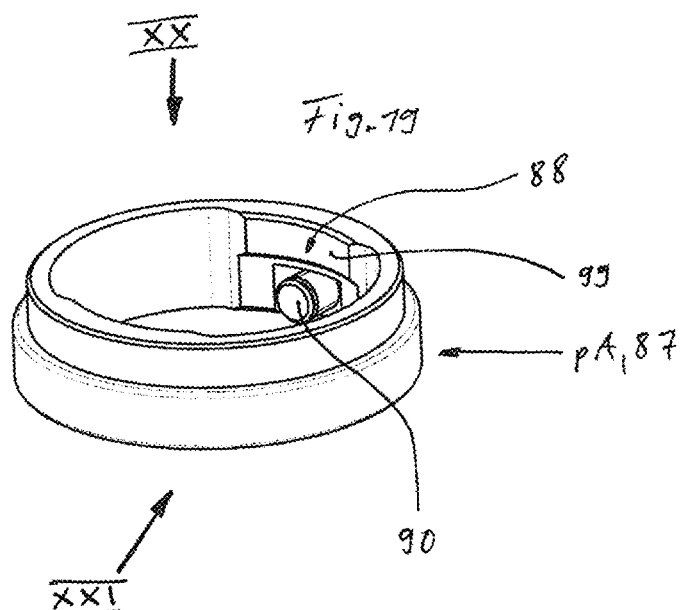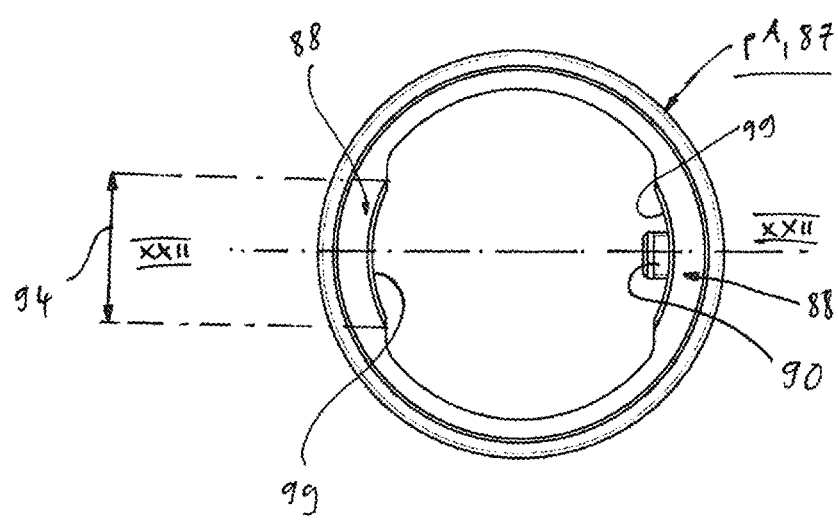

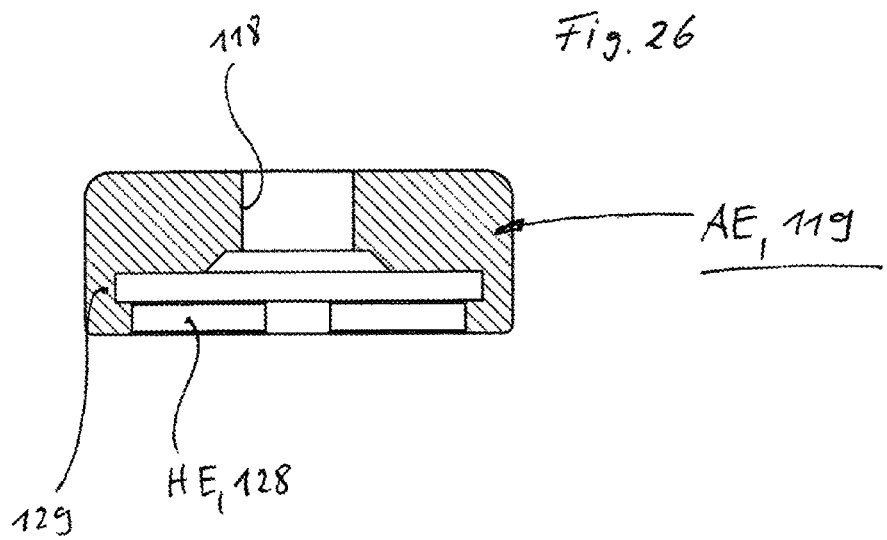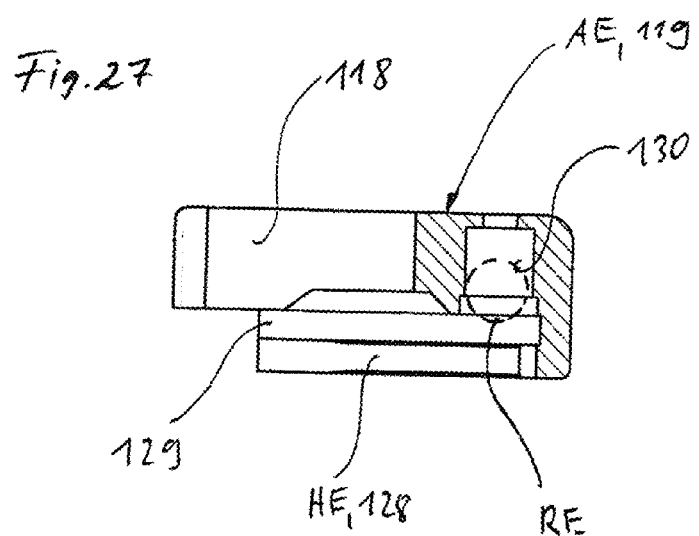

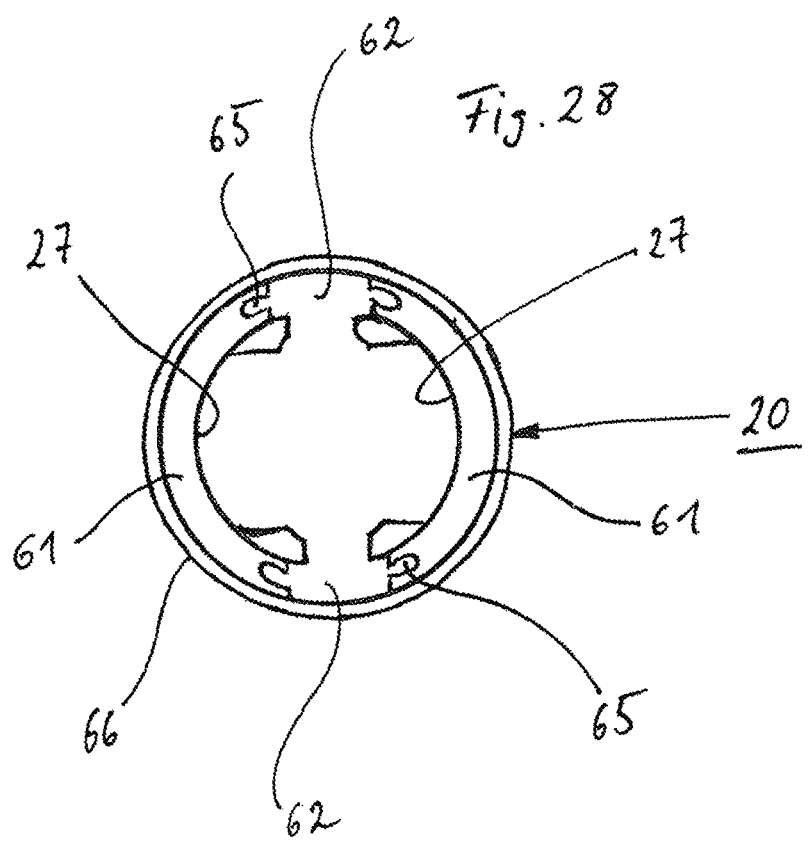

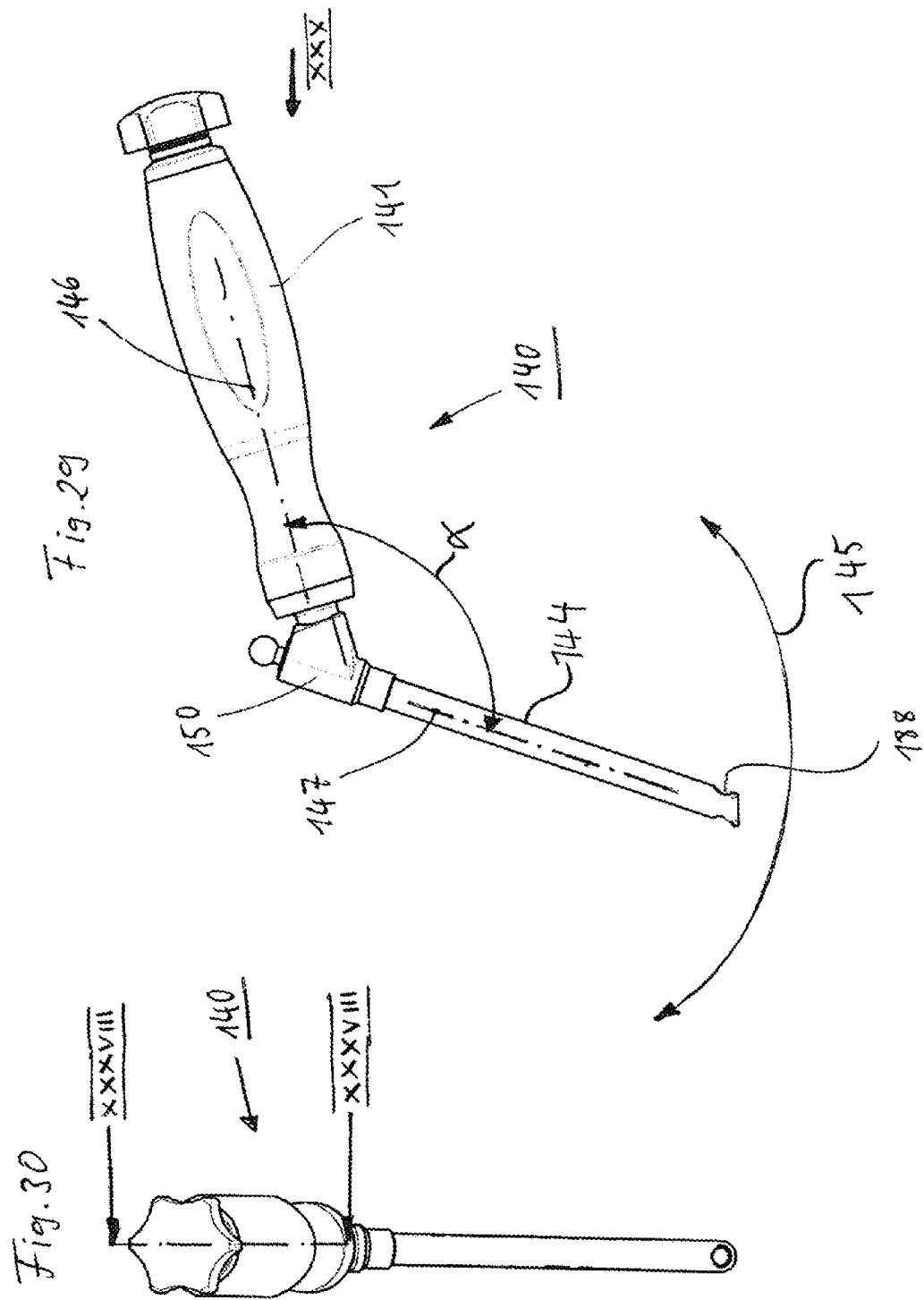

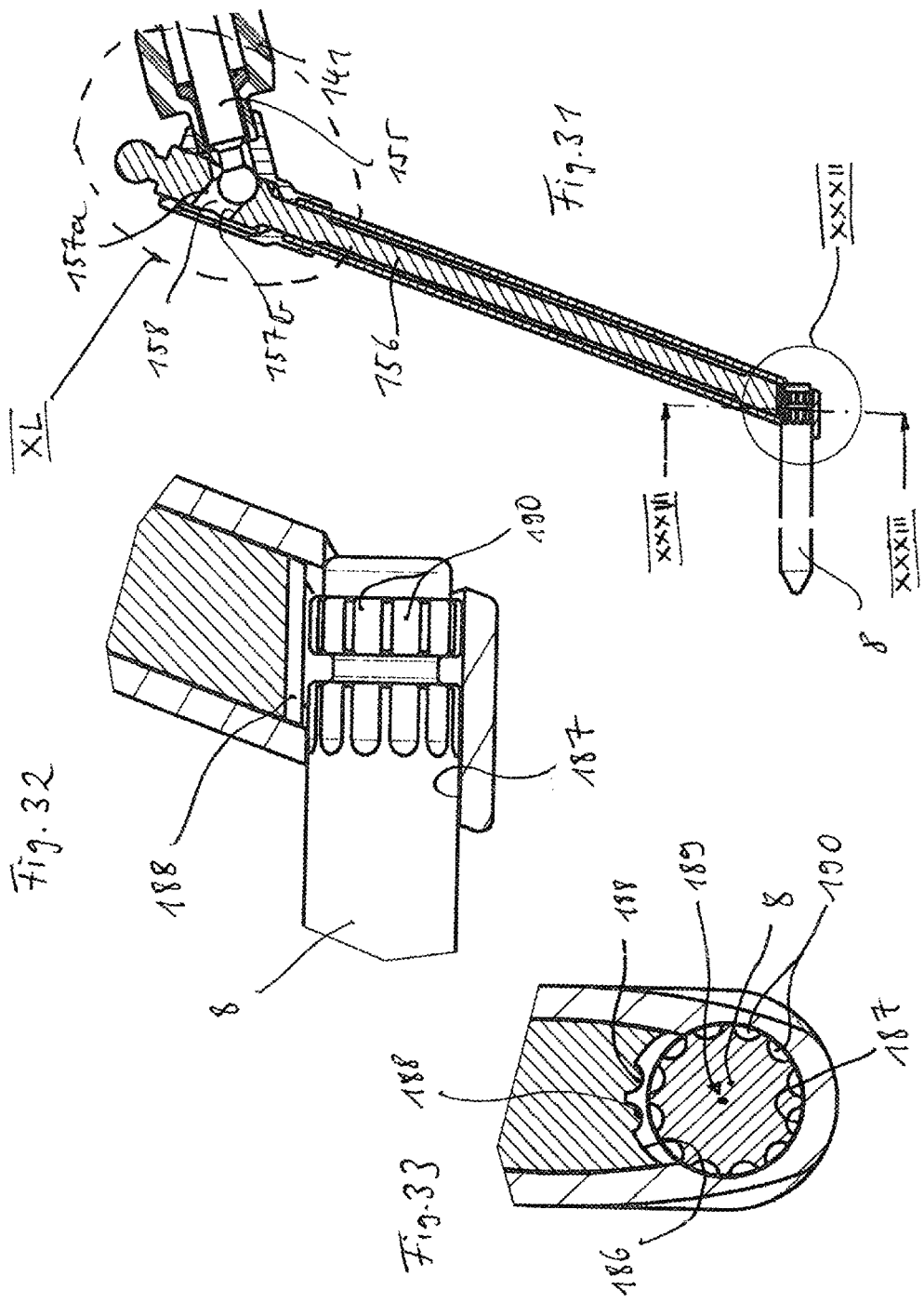

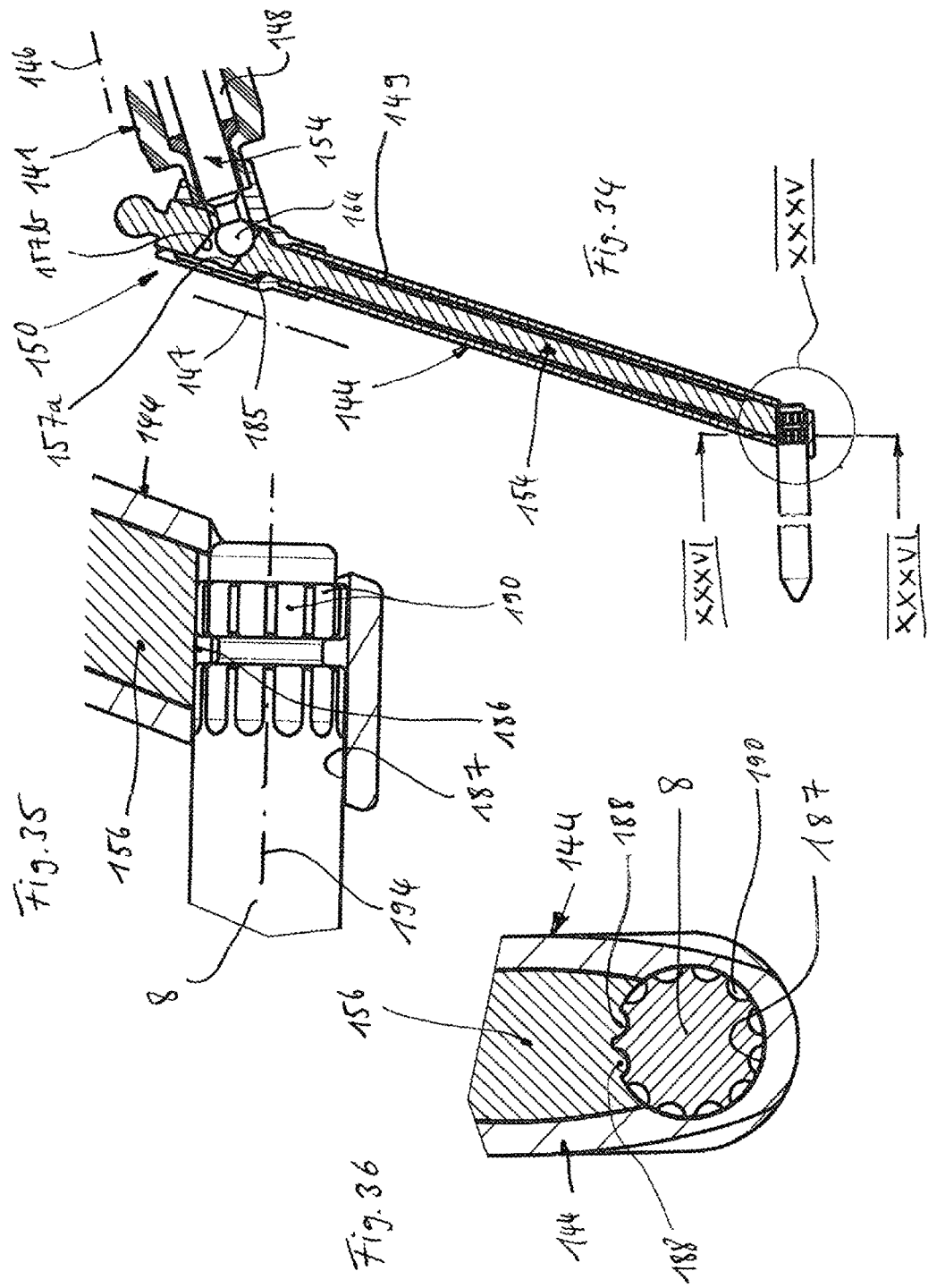

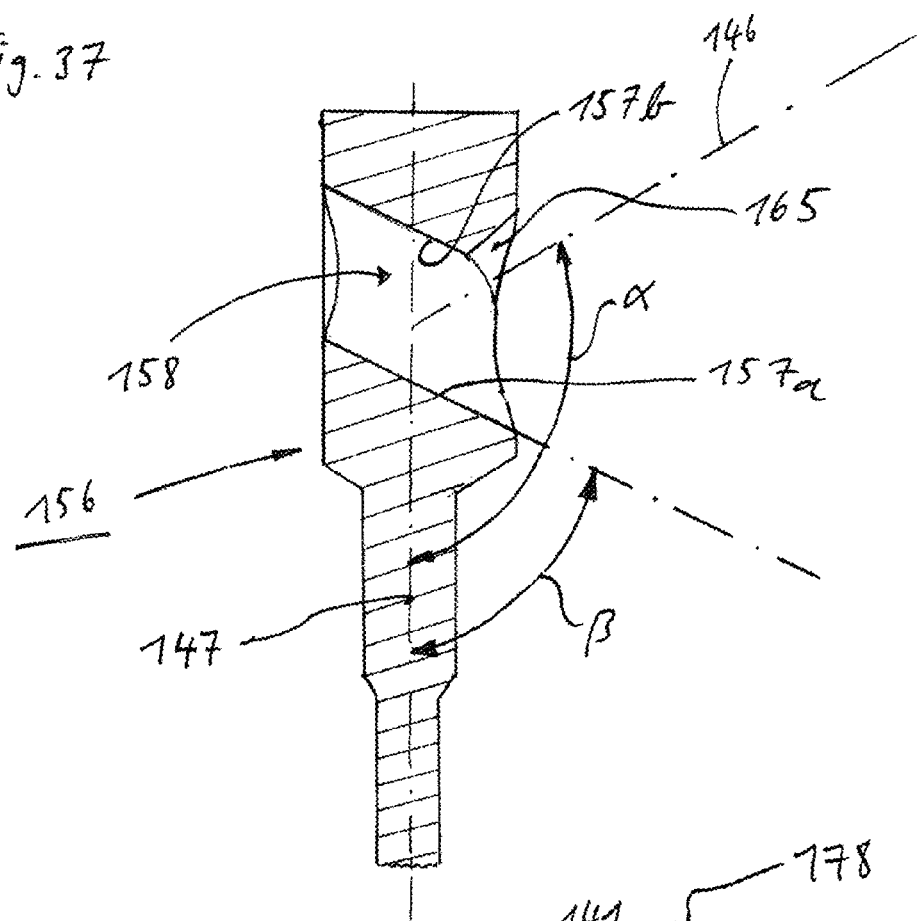
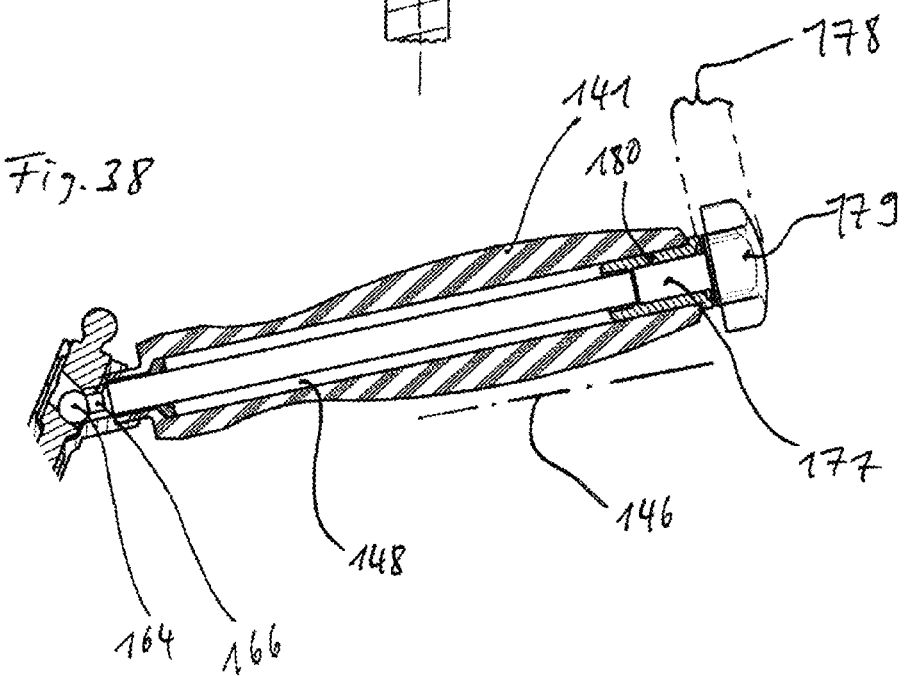

SET OF INSTRUMENTS FOR THE PERCUTANEOUS STABILIZATION OF THE SPINE WITH THE AID OF PEDICLE SCREWS AND RODS

The invention relates to an instrument set for percutaneous stabilization of the spinal column using pedicle screws and rods. This type of stabilization of the spinal column is not performed through an open incision on the back but instead through openings that are formed at points in the skin, one opening being needed for each pedicle screw that is to be implanted. First of all, a number of pedicle screws are introduced into the right and left pedicles of the spinal column, and the pedicle screws on each side are connected by a respective rod. The rods are inserted into a distally open recess in the head of the pedicle screws, i.e. a recess opening in a direction away from the patient's body, and they are fixed with the aid of fixing screws. On account of the restricted accessibility of the operating site, and because of the limited visual monitoring of the operation despite the use of imaging techniques, instruments for spinal column stabilization performed on the open back cannot be used, or can at best be used only to a limited extent.

The object of the invention is to make available an instrument set which allows percutaneous stabilization of the spinal column to be performed safely and reliably.

This object is achieved by an instrument set as claimed in claim 1. This instrument set comprises a screw manipulator through which a central cavity passes axially and which has a cylindrical sleeve and a slide. The wall of the cylindrical sleeve is divided into two first wall segments by two diametrically opposite and axially extending windows which open out in the proximal end face of the sleeve. The proximal ends of the first wall segments form grip elements which, during a screw manipulation, receive between them at least a longitudinal portion of the screw head. As a result of this design, the free ends or proximal ends of the wall segments, even in a relatively mechanically solid configuration, are able to bend open radially, like resilient tongues, at least slightly, such that the screw manipulator can be inserted in the axial direction, or with a joining movement extending in this direction, i.e. axially, through a skin opening or tissue opening on the patient's back and, with widening of the first wall segments, can be plugged onto the head. The diametrically opposite grip elements engage around the head, in other words the head protrudes at least with a longitudinal portion into a receiving space which is laterally limited by the proximal ends of the first wall segments or by the grip elements. The radial expansibility of the grip elements is particularly advantageous if a radially inwardly protruding locking element or form-fit element is present on the mutually facing inside surfaces of the grip elements, in particular a locking element or form-fit element produced integrally with the grip elements, which locking element or form-fit element engages in a preferably complementary recess in the outside of the head and thus ensures an axially and rotationally fixed connection between head and screw manipulator A further feature of the screw manipulator is the above-mentioned slide. The latter is held on the sleeve, displaceably in the axial direction of the screw manipulator, and thus connected to the first wall segments such that it secures these against moving radially apart, at least in a proximal end position of displacement. This design ensures that a screw head is clamped safely and firmly between the grip elements. Thus, in the proximal end position of displacement of the slide, a pedicle screw or the head thereof can be subjected, with the aid of the screw manipulator, to a force directed transversely with respect to the longitudinal axis of the screw, and a vertebra is thus reset, i.e. brought from a dislocated position to a correct position.

Further advantageous embodiments of the invention will become clear from the following description, in which reference is made to the attached drawings. In the drawings.

Figure 12:
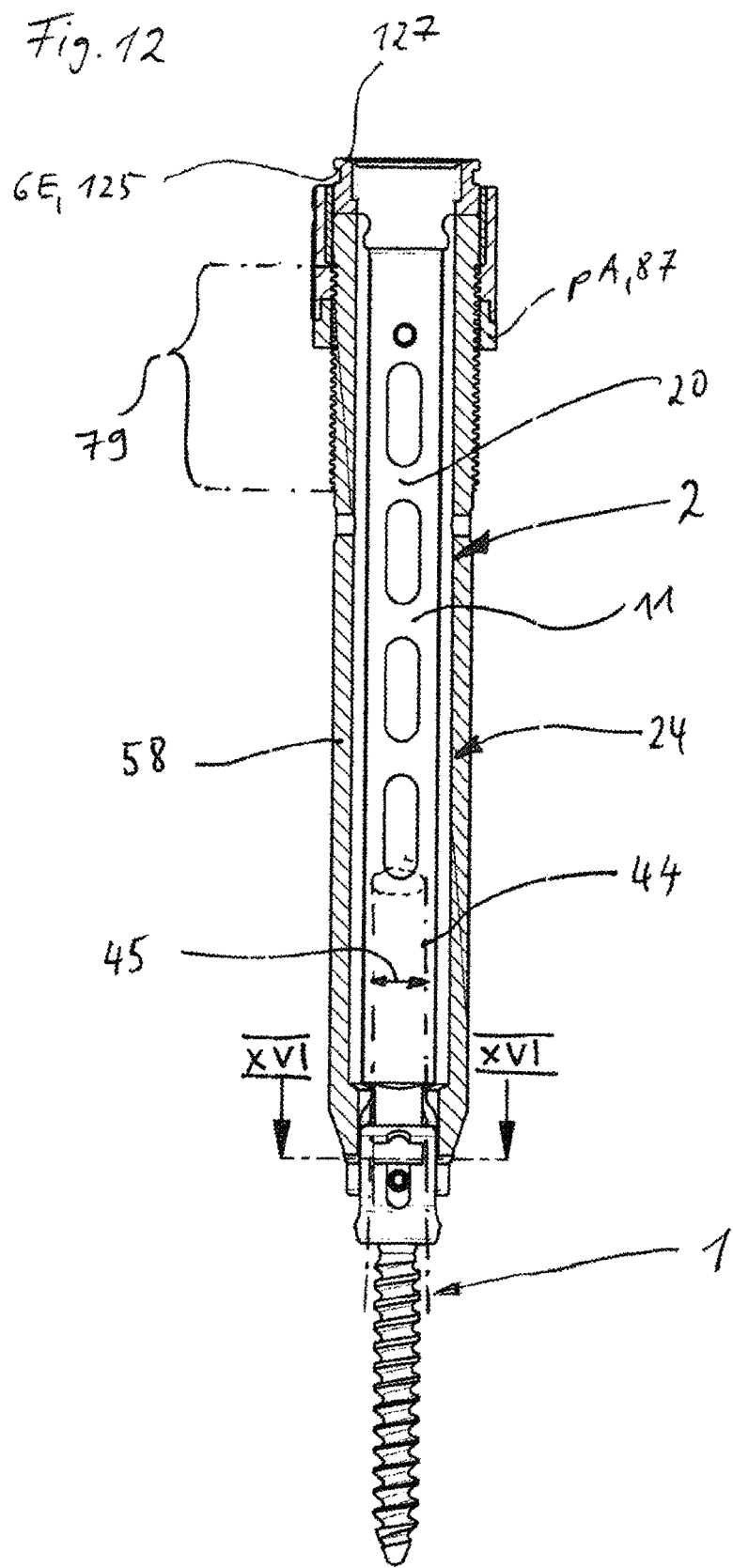
Figure 21:
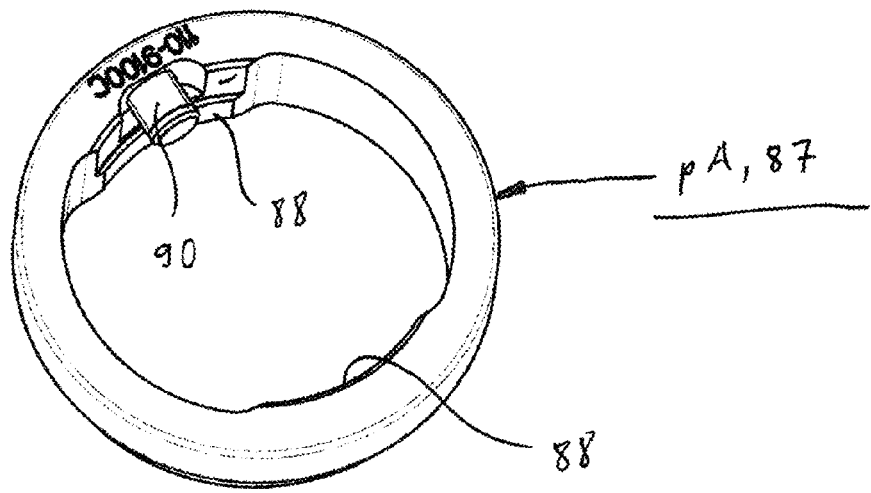
Figure 22:
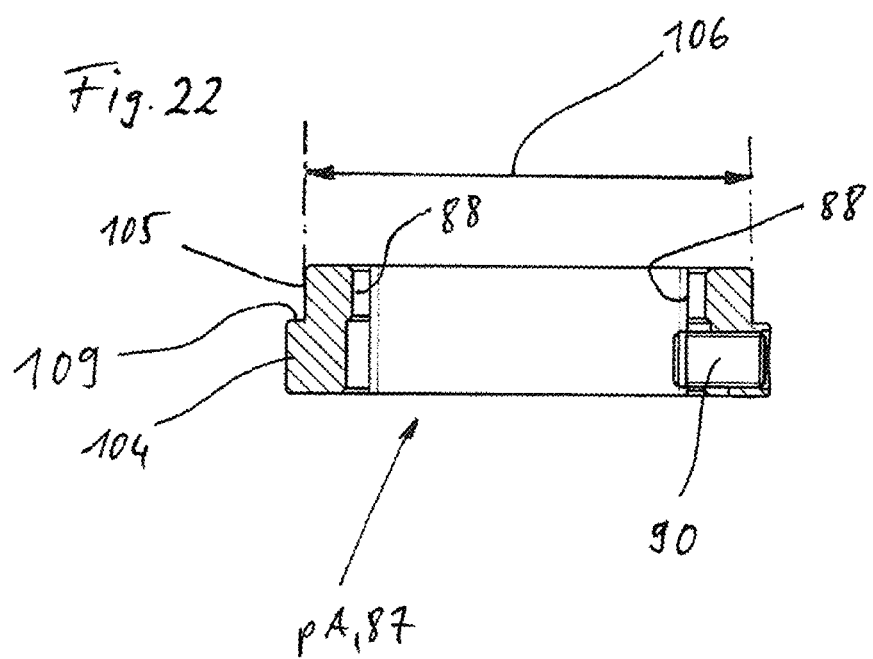
Figure 23:
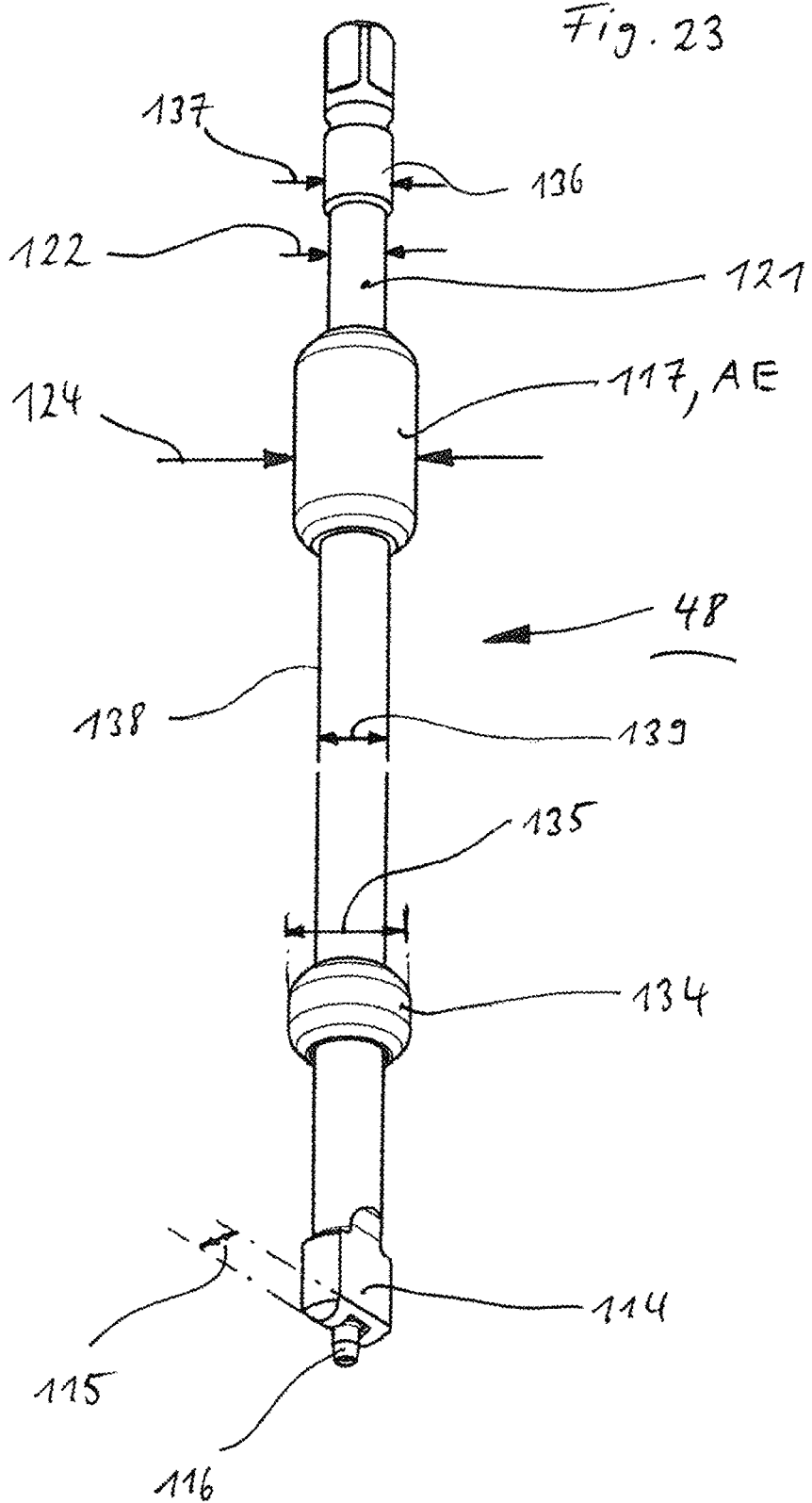
Figure 24:
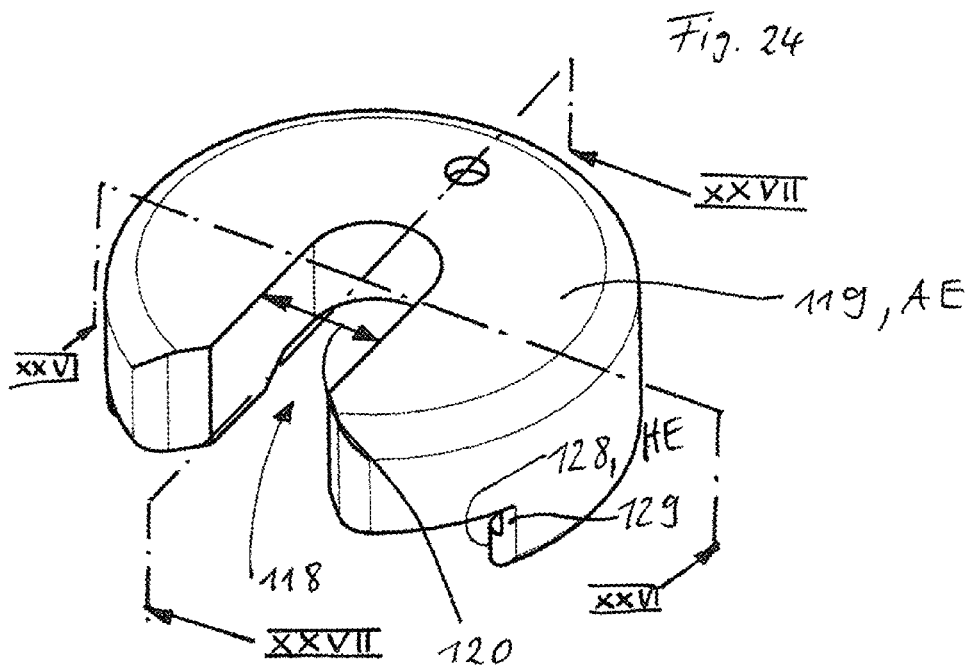
Figure 25:
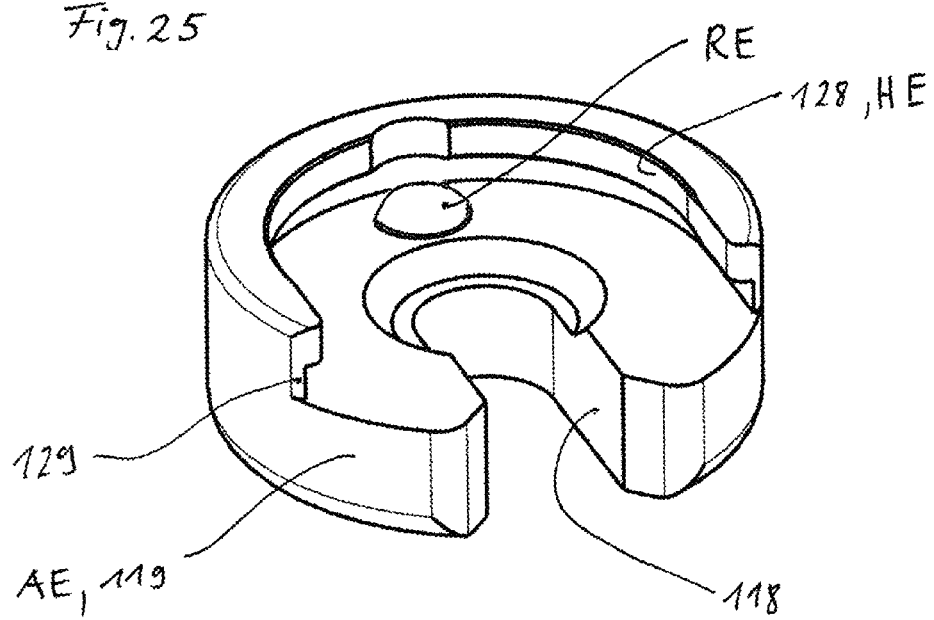
Figure 39:
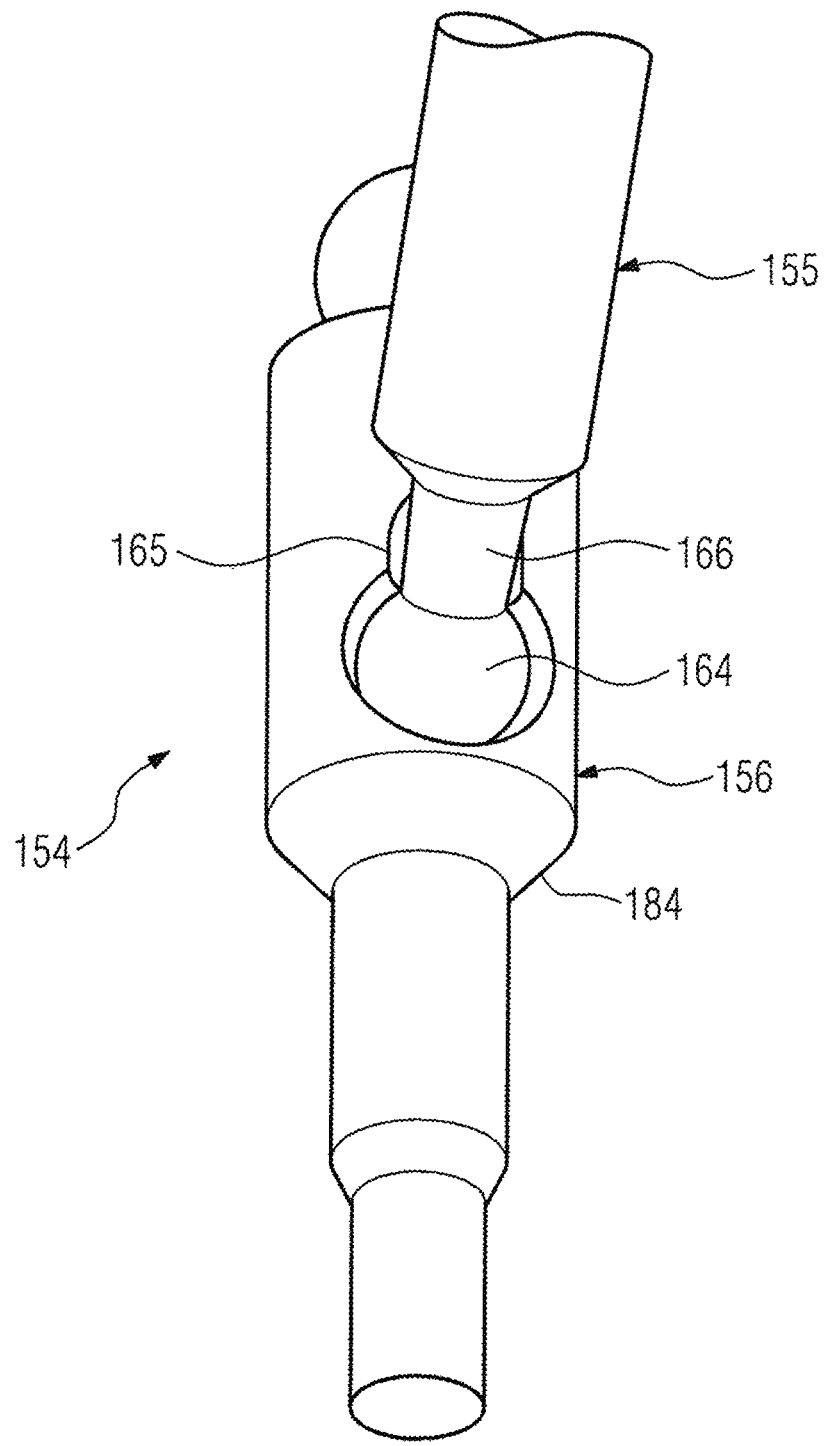
Figure 40:
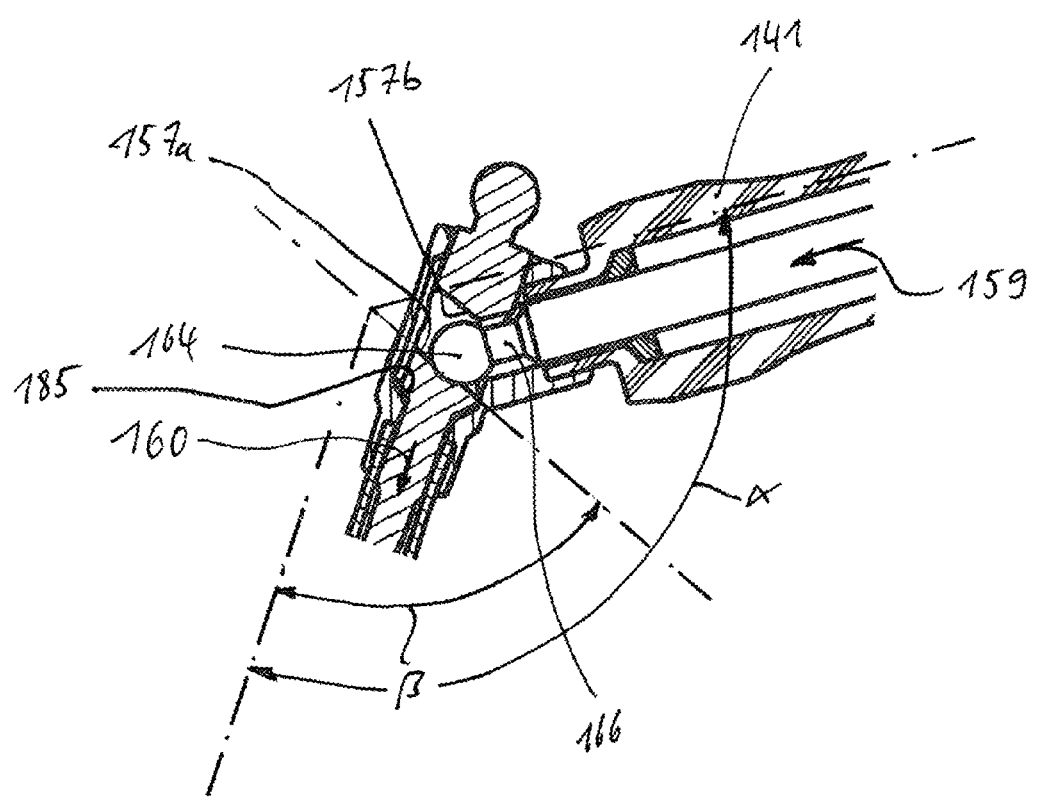

FIG. 2 shows vertebral bodies of a spinal column that have been stabilized using rods and pedicle screws, the vertebrae being depicted in a highly schematic form, FIG. 3 shows a side view of a screw manipulator, which comprises a sleeve, a slide and an adjusting nut, FIG. 4 shows a side view of the screw manipulator, which has been rotated 90° about its central longitudinal axis in relation to FIG. 3, FIG. 5 shows a longitudinal section through the screw manipulator according to line V-V in FIG. 4, FIG. 6 shows a side view of the sleeve of the screw manipulator, FIG. 7 shows a side view of the sleeve, which has been rotated 90° about its central longitudinal axis in relation to FIG. 6, FIG. 8 shows a longitudinal section according to line VIII-VIII in FIG. 6, FIG. 9 shows a perspective view of the slide of the screw manipulator, FIG. 10 shows a partially cutaway side view of a screw manipulator holding a pedicle screw, FIG. 11 shows the screw manipulator from FIG. 10, but rotated 90° about its central longitudinal axis, FIG. 12 shows a longitudinal section through the screw manipulator holding a pedicle screw, according to line XII-XII in FIG. 11, FIG. 13 shows a screw manipulator holding a pedicle screw, with a screw driver inserted into the screw manipulator, FIG. 14 shows the screw manipulator from FIG. 13, but rotated 90° about its central longitudinal axis, FIG. 15 shows a longitudinal section according to line XV-XV in FIG. 13, FIG. 16 shows a cross section according to line XVI-XVI in FIG. 12, FIG. 17 shows the detail XVII from FIG. 15 in an enlarged view, FIG. 18 shows the adjusting nut of the screw manipulator in a perspective view, FIG. 19 shows a perspective view of a proximal abutment serving to axially fix the adjusting nut on the screw manipulator and designed as an abutment ring, FIG. 20 shows the abutment ring in a plan view, in the direction of the arrow XX in FIG. 19, FIG. 21 shows the abutment ring in the direction of the arrow XXI in FIG. 19, FIG. 22 shows a cross section according to line XXII-XXII in FIG. 20, FIG. 23 shows the screwdriver in a perspective view, FIG. 24 shows a perspective view of a locking element serving to axially fix the screwdriver on the screw manipulator, FIG. 25 shows a perspective view of the locking element, but seen from another angle, FIG. 26 shows a cross section according to line XXVI-XXVI in FIG. 24, FIG. 27 shows a cross section according to line XXVII-XXVII in FIG. 24, FIG. 28 shows a plan view of the distal end face of the sleeve, in the direction of the arrow XXVIII in FIG. 6, FIG. 29 shows a side view of a gripping tool serving to manipulate a rod and comprising a drive element and a driven element, FIG. 30 shows the gripping tool seen in the direction of the arrow XXX in FIG. 29, FIG. 31 shows a section through the gripping tool from FIG. 30, the section plane running in the plane of the paper, FIG. 32 shows the detail XXXIII from FIG. 31 on an enlarged scale, FIG. 33 shows a section according to line XXXIII-XXXIII in FIG. 31, FIG. 34 shows a view corresponding to FIG. 31, but with the gripping tool located in another operating situation, FIG. 35 shows the detail XXXV from FIG. 34 on an enlarged scale, FIG. 36 shows a section according to line XXXVI-XXXVI in FIG. 34, FIG. 37 shows a partial longitudinal section through the drive tool, FIG. 38 shows a section according to line XXXVIII-XXXVIII in FIG. 30, FIG. 39 shows a partial perspective view of the drive element and driven element, FIG. 40 shows the enlarged detail XL from FIG. 31.

Figure 1A:
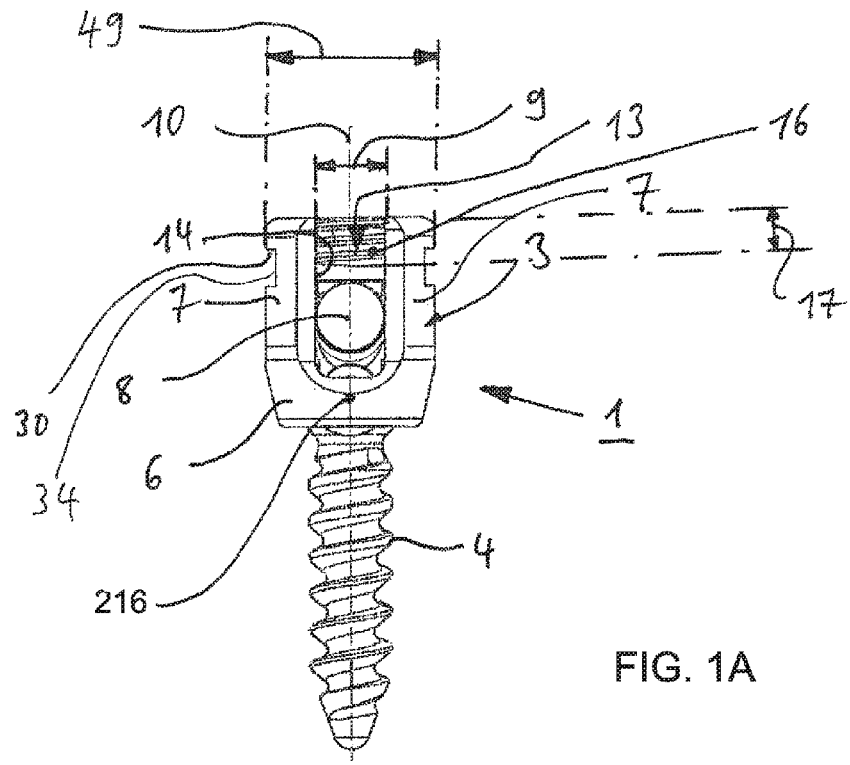
FIG. 1A shows a pedicle screw in a side view.
Figure 1B:
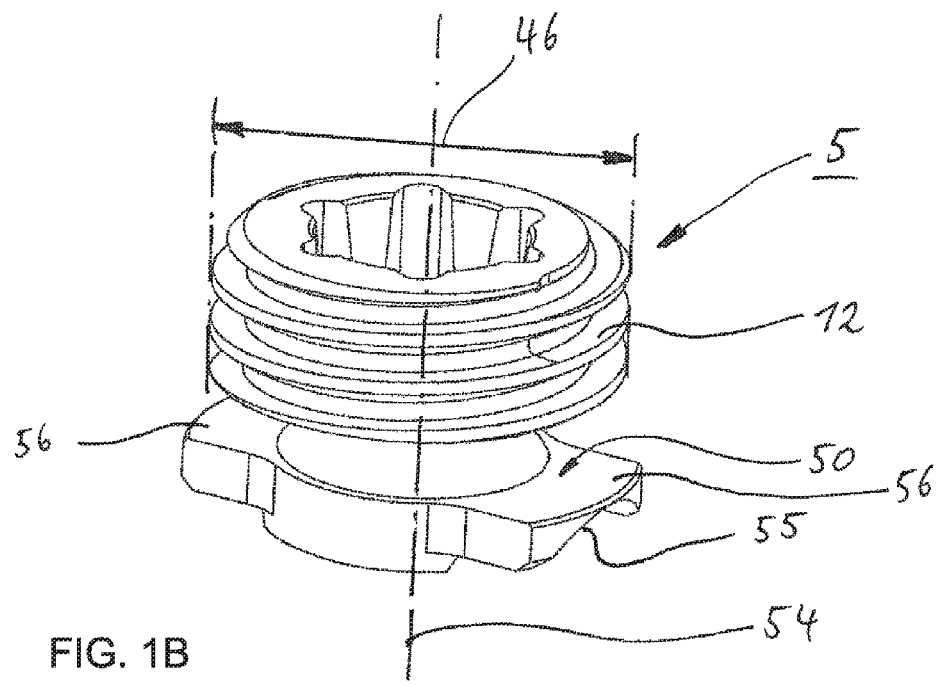
FIG. 1B shows a fixing screw in a perspective view.

FIG. 1 shows an example of a pedicle screw 1 which, during a procedure for percutaneous stabilization of the spinal column, can be maneuvered with the aid of the screw manipulator 2 according to the invention. The pedicle screw 1 is composed basically of a screw head 3, a screw shank 4 provided with a thread, and a fixing screw 5. On its lower end facing the screw shank 4, the screw head 3 has a head base 6, on which two distally extending wall portions 7 are integrally formed. The words proximal and distal as used here, and further below in connection with the definition of directions and positions, refer to the situation during an operation. The wall portions 7 lie diametrically opposite each other, extend in each case only about a portion of the circumference of the head base 6 and form a lateral boundary for a recess 13, which serves to receive a rod 8 and opens out in the distal end face of the screw head 3. The breadth 9 of the spaces 14 present between the side edges of the wall portions 7 extending parallel to the central longitudinal axis 10 of the screw head 3 corresponds substantially to the diameter 15 of a rod 8 (FIG. 2) or is slightly larger than this.

The screw shank 4 is either rigidly connected to the screw head 3, held on the screw head 3 so as to be pivotable about an axis 216, as is the case in the screw example shown here, or mounted multi-axially on the screw head 3. The fixing screw 5, serving to clamp the rod 8 in the recess 13, is inserted into the recess 13 from the direction of the distal end face of the screw head 3. It has roughly the shape of a grub screw and comprises an outer thread 12, which cooperates with an inner thread 16 arranged on the inside surface of the wall portions 7. The inner thread 16 extends at least approximately away from the free end of the wall portions 7 in the proximal direction, wherein its thread length 17, i.e. its axial extent, is dimensioned, for example, such that it ends at an axial distance before the bottom of the recess 13.

In a procedure for stabilization of the spinal column involving three vertebral bodies, for example, six pedicle screws and two rods 8 are needed. The pedicle screws are screwed into the right and left pedicles of the vertebral bodies 18 with the aid of a screwdriver 48 inserted axially into the screw manipulator, as is explained in greater detail below. The recesses 13 of the screw heads 3 assigned to one side are oriented such that the spaces 14 all point substantially in one and the same direction, which is easier to ensure if screw head 3 and screw shank 4 are connected to each other in an articulated manner. If one or more vertebral bodies 18 of the area of the spinal column to be stabilized are dislocated, the screw manipulator gripping the screw head 3 is used to reset the vertebral body 18, with suitable pivoting of the pedicle screws 1. The insertion of the rods 8 into the recesses of the pedicle screws 1 is also facilitated by the screw manipulator (see further below).

The screw manipulator 2 has a central cavity 11 passing axially through it and comprises a cylindrical sleeve 20 and a slide 24. The cavity 11 of the screw manipulator is shaped and dimensioned in the radial direction in such a way that it can receive a fixing screw 5 that is to be screwed in so as to fix a rod 8 lying in the distally open recess 13 of a pedicle screw 1, i.e. such that the fixing screw 5 can be inserted into the cavity 11 of the screw manipulator 2 from the direction of the distal end thereof and, for example with the aid of a screwdriver, can be transported to the proximal end of said manipulator and screwed into the recess 13.

The wall of the sleeve 20 is divided into two first wall segments 27 by two diametrically opposite and axially extending windows 26 which open out in the proximal end face of the sleeve 20. The proximal ends of the first wall segments 27 form grip elements 28 which, during a screw manipulation, receive between them at least a longitudinal portion of the screw head 3 of a pedicle screw 1 and clamp the latter. The screw manipulator 2 is dimensioned in the axial direction such that, during its manipulation, for example for resetting a vertebral body 18, it can be grasped in one hand and the forces needed for the resetting can be applied. For example, the manipulator is dimensioned such that the first wall segments 27 have a length of approximately 15 cm. The first wall segments 27 are designed such that they are radially expandable to a certain extent or can be moved radially away from each other and, by virtue of elastic restoring forces, can return to their starting position. Therefore, the grip elements 28 can be easily plugged onto the screw head 3. Such radial expansibility or flexibility of the first wall segments 27 is particularly advantageous if an engage-behind element 29 protrudes radially inward on the inside surfaces of the grip elements 28 and engages behind a radially inwardly projecting mating surface 30 (FIGS. 1, 2 and 10) which is present on the wall portions 7 of the screw head 3 and faces toward the screw shank 4. For example, the mating surface 30 is a wall extending in the circumferential direction of the screw head 3 and forming part of a recess 34 introduced into the wall portions 7 of the screw head 3. This design substantially increases the strength with which a screw head 3 can be held by the grip elements 28, in particular when resetting a vertebral body 18.

A moving apart of the grip elements 28, which is advantageous when plugging the screw manipulator onto a screw head 3 but not when manipulating the pedicle screw, for example during the resetting of a vertebral body 18, is prevented by the slide 24. The latter is connected to the first wall segments 27, such that it secures these against radially moving apart, at least in a proximal end position of displacement. The way in which this is achieved in a preferred embodiment variant is explained in more detail below.

Whereas spinal column stabilization performed on the open back involves a rod 8 being inserted from above into the head recesses 13 of a row of pedicle screws 1, the percutaneous operating technique involves the rod 8 being inserted through a surgical opening into a recess 13 of the pedicle screw assigned to the surgical opening, and then being advanced in the longitudinal direction of the spinal column such that it passes through the recesses 13 of pedicle screws following on in the longitudinal direction of the rod. If a rod 8 is positioned too close to the end face of the head, for example on account of its being pressed in the distal direction by tissue, the screwing of the fixing screw 5 into the recess 13 is impeded or made impossible, since the outer thread 12 of the fixing screw 5 cannot engage, or can engage only insufficiently, in the inner thread 16 of the pedicle screw 1. In order to avoid this problem, the slide 24 has, at its proximal end, at least one holding-down element 35 with which, in the proximal end position of displacement of the slide 24, the rod 8 inserted into a recess 13 is held inside the recess groove, such that the fixing screw 5 can be screwed without obstruction into the screw head 3 and the rod 8 can be fixed.

This further function of the slide 24 is ensured in particular if the at least one holding-down element 35, in the proximal end position of displacement of the slide 24, is at an axial distance 38 from the front face 25 of the sleeve 20, or of the first wall segments 27, that is smaller than the insertion depth 39 to which the screw head 3 protrudes axially into a receiving space 37 of the screw manipulator 2 limited laterally by the grip elements 28 (see FIG. 10). It is particularly expedient if the axial distance 38 is less than or equal to the difference D of the insertion depth 39 of the screw head 3 and the thread length 17 of the inner thread 16. The fixing screw 5 can then firstly be screwed practically completely into the inner thread 16 before, toward the end of the screwing-in process, the fixing screw 5 impacts the rod 8 and presses the latter against the bottom of the recess 13.

An obstruction to screwing the fixing screw 5 into the screw head 3 with the aid of a screwdriver (not shown) inserted into the cavity 11 of the screw manipulator 2 is prevented by the fact that the at least one holding-down element 35 is arranged outside an imaginary cylinder 44 which extends coaxially with respect to the central longitudinal axis 40 of the sleeve 20 and of which the diameter 45 (FIG. 12) substantially corresponds to the core diameter of the inner thread 16 of the screw head 3 or to the diameter 46 of the outer thread 12 of the fixing screw 5. If the holding-down element 35 is arranged further radially to the outside, that is to say outside an imaginary cylinder 40 whose diameter 45 corresponds to the external diameter 49 of the screw head 3, it is possible to use a fixing screw which, on its underside, has a pressure plate 50 protruding beyond the outer thread 12 of the screw and acting on the circumferential surface of the rod 8. The pressure plate 50 is preferably connected to the fixing screw 5 such that it is rotatable about the central longitudinal axis 54 thereof and is also tiltable in each rotation position with respect to this axis. On its proximal side, the pressure plate 50 has a trough-shaped recess 55 designed to complement the surface curvature of the rod 8. The pressure plate 50 protrudes beyond the outer thread 12 of the fixing screw 5 with two diametrically opposite extensions 56, the trough-shaped recess extending into the proximal side of the extensions 56.

The slide 24 is a hollow cylinder whose wall is divided into two second wall segments 58 by two diametrically opposite and axially extending windows 57 which open out in the proximal end face of the hollow cylinder. The second wall segments 58 are guided in an axially displaceable manner in the windows 26 of the sleeve 20. The proximal end faces each form a holding-down element 35. In the proximal end position E, the holding-down elements 35 assume the above-described position relative to the end face 25 of the sleeve 20. The curvature of the first and second wall segments 27, 58 is chosen in such a way that their outer surfaces run in a common cylindrical envelope surface, thereby resulting overall in a circular circumferential shape of the screw manipulator 2. Moreover, the first wall segments 27 extend over a greater arc length than the second wall segments 58. This dimensional relationship is advantageous since, for example when resetting a vertebral body 18, relatively great forces have to be introduced into the first wall segments 27 or into the grip elements 28 formed by the free ends of the wall segments 27. The second wall segments 58 also have such a length that, in the proximal end position of displacement of the slide 24, the screw manipulator 2 as a whole is a hollow cylinder closed in the circumferential direction. Recesses 59 can pass through the first wall segments 27, for example to reduce weight. The same is also conceivable for the second wall segments 28.

In a preferred embodiment variant, a radial expansion of the grip elements 28 in the proximal end position E of displacement of the slide 24 is brought about by the fact that an axially extending rib 64 protrudes from the side edges of the second wall segments 58 facing in the circumferential direction 60 of the screw manipulator 2, and, in the side edges of the first wall segments 27, a groove 65 is present into which the ribs 64 engage axially displaceably with a form fit effective in the circumferential direction 60. Thus, the nearer the slide 24 comes to its proximal end position E, i.e. the shorter the longitudinal portions of the first wall segments 27 not held by the slide 24, the smaller is the radial expansibility. In the proximal end position E, there is no longer any radial expansibility, such that the grip elements 28 clamp the screw head 3 between them with great strength and secure it in the receiving space 37.

The distal ends of the first wall segments 27 are connected to each other via a first cylinder portion 66 and the distal ends of the second wall elements 58 are connected to each other via a second cylinder portion 67. The first and second wall elements 27, 58 are each designed integrally with the respective cylinder portion, wherein they are connected to the proximal end of the cylinder portions. The internal diameter 68 (FIG. 8) of the first cylinder portion 66 is greater than the external diameter 69 (FIG. 9) of the second cylinder portion 67. The axial lengths of the cylinder portions are dimensioned such that the second cylinder portion 67 protrudes beyond the first cylinder portion 66 with an axial overshoot 70 (FIG. 5). An annular groove 74 is present in the circumferential surface of the axial overshoot 70.

The slide 24 can be plugged into the sleeve 20 from the direction of the distal end face of the latter. As can be seen in particular from FIG. 8 and FIG. 28, the first wall areas 27 of the sleeve 20 are offset radially inward with respect to the outer circumferential surface of the first cylinder portion 66, wherein they merge via a shoulder 61, which is preferably part of a distally widening cone surface, into the inner wall of the first cylinder portion 66. In the end position E of displacement, the slide bears on the shoulder 61 via the proximal end face of the second cylinder portion, which is optionally designed complementing the cone shape of the shoulder 61. The spaces 62 extending in the circumferential direction between the shoulders 61 receive the second wall segments 58 of the slide 24.

The axial movement of the slide 24 relative to the sleeve 20 takes place via a helical gearing. This is achieved by the fact that an outer thread 75 protrudes from the outer surface of the second wall segments 58 of the slide 24 and cooperates with an inner thread 76 of an axially fixed but rotatable adjusting nut 77 that engages coaxially around the sleeve 20.

The external diameter 78 (FIG. 4) of the outer thread 75 is smaller than the internal diameter 68 (FIG. 8) of the second cylinder portion 66 of the sleeve 20. By virtue of this dimensional relationship, the slide 24 can be pushed unimpeded through the first cylinder portion 66. The outer thread 75 of the slide 24 does not extend over the entire length of the second wall segments 58, but instead only over a longitudinal portion 79 (FIG. 12) adjoining the second cylinder portion 67. The longitudinal portion 79 corresponds approximately to a quarter of the total length of the second wall segments 58.

The inner thread 76 extends only over a partial area of the total axial length of the adjusting nut 77. A threadless inner wall area 80 is present between the inner thread 76 and the distal end face of the adjusting nut 77, its internal diameter 84 being slightly greater than the external diameter 85 of the first cylinder portion 66 of the sleeve 20. The inner wall area 80 is dimensioned in the axial direction in such a way that it receives or engages substantially completely around the first cylinder portion 66 or at least a longitudinal portion thereof.

The adjusting nut 77 is axially fixed on the screw manipulator 2 by means of the fact that a proximal abutment element (pA) (e.g. FIG. 3) and a distal abutment element dA (FIG. 7) protrude, at an axial distance from each other, from the outer surfaces of the first wall segments 27, which abutment elements (pA, dA) enclose between them, and radially overlap, a counter-abutment element (GA) (FIG. 18) that protrudes radially inward from the inner surface of the adjusting nut 77 and is formed by the inner thread 76. The distal abutment element dA is formed by the first cylinder portion 66, wherein the latter has a shoulder 86 protruding radially beyond the outer surfaces of the first wall segments 27. The proximal abutment element pA is an abutment ring 87 which engages around the sleeve 20, or the outer circumference of the screw manipulator 2, and which is releasably connected to the first wall segments 27 in an axially fixed manner. The abutment ring 87 has a projection 88 extending in the circumferential direction 60 and protruding from its inner wall, and it engages with this projection 88 in a likewise circumferentially extending groove 89 in the outer surfaces of the first wall segments 27. A releasable rotational and axial fixing of the abutment ring 87 is effected with the aid of a screw 90, which passes radially through the abutment ring 87 and which, in the tightened state, presses against the outer surface of the first wall segments 27.

The proximal end of the sleeve 20, i.e. the end comprising the grip elements 28, is a radially narrowed longitudinal portion 96, which merges via a cone portion 97 into the main area 98 of the sleeve 20 extending as far as the first cylinder portion 66. The breadth 94 of the projection 88, of which the inner wall 99 is part of a cylinder surface, is smaller than the inside width 100 of the windows 26 in the main area 98 of the sleeve 20. When assembling the screw manipulator 2, the abutment ring 87 can therefore be pushed onto the main area 98 when it is located in a rotation position in which its projections 88 are located in the circumferential portion of the sleeve 20 occupied by the windows. The projections 88 extend in the axial direction away from the distal end face of the abutment ring 87, but only over a partial length of the abutment ring 87. The screw 90 passes through an inner wall area extending proximally away from one of the two projections 88.

The abutment ring 87 has a proximal longitudinal portion 104 and, compared to the latter, a radially narrowed longitudinal portion 105. Its external diameter 106 is slightly smaller than the internal diameter 107 of an inner wall area 108 of the adjusting nut 77 proximally adjoining the inner thread 76 (FIGS. 17 and 18). The axial length of the narrowed longitudinal portion 105 is chosen such that the latter engages fully in the inner wall area 108 of the adjusting nut 77. The adjusting nut 77 bears with its proximal end face on a radial shoulder 109, which forms the transition between the longitudinal portions 104 and 105.

The instrument set further comprises the screwdriver 48 already mentioned above. This screwdriver 48 is rod-shaped and is insertable into the central cavity 19 of the screw manipulator 2 and, during use, is inserted therein. Arranged at the proximal end of the screwdriver is a rotation actuation element 114 that can be plugged into the recess 13 of the screw head 3 for joint rotation therewith. This rotation actuation element has more or less the shape of a plate, of which the breadth 115 is slightly smaller than the breadth 9 of the spaces 16 of the screw head 3. Optionally, a pin 116 protrudes axially from the proximal end face of the screwdriver 48 or of the rotation actuation element 114, which pin 116 is provided in order to be inserted into a bore 111 (FIG. 16) in the distal end of the screw shank 4 and thereby fix the screw shank in a coaxial orientation with respect to the central longitudinal axis 10 of the screw head 3.

To ensure that the screwdriver 48 is held reliably in the recess 13 of the screw head 3 or protrudes to a sufficient depth into the recess 13, a stop mechanism AE is provided (see FIG. 23 et seq.) with which the screwdriver 48 inserted into the cavity 11 of the screw manipulator 2 is held in a corresponding axial target position. For this purpose, the stop mechanism AE preferably comprises a projection 117 protruding from the circumferential surface of the screwdriver 48, and a stop element which radially overlaps the projection 117 in the target position of the screwdriver 48 and is axially fixed relative to the screw manipulator, which stop element is designed substantially as a disk 119. The axial position of the projection 117 on the screwdriver 48 is chosen such that the radial overlap of the projection 117 by the stop element can be produced only when the screwdriver 48 is located in its target position.

The projection 117 extends about the entire circumference of the rod-shaped screwdriver 48, i.e. is designed as an annular projection. By virtue of this design, the interaction with the stop element is possible independently of the respective rotation position of the screwdriver 48 relative to its central longitudinal axis. The stop element AE is preferably a disk 119, in particular a circular disk, with a radial groove 118. The radial groove 118 opens into the edge of the disk 119, such that the latter can be plugged onto the screwdriver 48 from the side or in the radial direction. Moreover, it extends so far radially inward that the disk 119 is engaged centrally by the screwdriver. The inside width 120 of the radial groove 118 is greater than the thickness or the diameter 122 of a longitudinal portion 121 of the screwdriver 48 extending distally from the projection 117. However, the inside width 120 is smaller than the dimension of the projection 117 in a direction extending transversely with respect to the central longitudinal axis of the screwdriver 48. In the case of an annular projection 117, the inside width 120 of the radial groove 118 is therefore smaller than the diameter 124 of the projection 117. A releasable, axially fixed connection between the screw manipulator 2 and the disk 119 is obtained via a locking connection, effective in the radial direction, i.e. a direction extending at right angles to the central longitudinal axis 40 of the screwdriver 48, between the disk 119 and the screw manipulator 2. For this purpose, a resiliently mounted locking element RE, for example in the form of a ball, protrudes from the proximal side of the disk 119. The locking element RE is held in a bore 130 opening into the proximal side of the disk 119 and is designed protruding from this. The locking element RE engages in an annular groove 127 (FIGS. 9 and 17) in the distal end face of the slide 24.

An engage-behind element HE is arranged on the proximal side of the disk 119, which engage-behind element HE, in order to axially stop the screwdriver 48 on the screw manipulator 2, can be plugged onto the screw manipulator 2 in a joining direction extending transversely with respect to the central longitudinal axis 40 of the screwdriver, thereby engaging in the plugged-on state behind a counter-element GE arranged on the screw manipulator 2. The counter-element GE is the groove wall 125, facing toward the proximal end of the screw manipulator 2, of the annular groove 74 present in the second cylinder portion 67. The engage-behind element HE is, for example, a flange 128 extending in a U shape and arranged at an axial distance from the proximal side of the disk 119. The flange 128 opens in the same direction as the radial groove 118 and is formed integrally on a U-shaped skirt 129 which extends away from the proximal side of the disk 119. In addition to its stop function, the projection 117 also has the task of holding the screwdriver securely against tilting in the interior 11 of the screw manipulator 2. Its dimensions in a direction extending transversely with respect to the central longitudinal axis 40 of the screwdriver 48 are chosen such that there is no play or only slight play between the projection 117 and the inside wall of the interior 11. Likewise for the stated purpose, a further projection 134 is formed integrally on the screwdriver 48, specifically at an axial distance in the proximal direction from the projection 117. The projection 134 is designed, for example, as an annular projection, its diameter 135 corresponding to the diameter 124 of the projection 117.

The screwdriver 48 has, finally, another for example annular projection 136, which is arranged on the longitudinal portion 121 at an axial distance from the projection 117. The dimension of the projection 136 in a direction extending transversely with respect to the central longitudinal axis of the screwdriver 48, i.e. its diameter 137, is smaller than the diameter 124 of the projection 117 but greater than the inside width 120 of the radial groove 118 of the stop element AE or of the disk 119. The longitudinal portion 138 extending between the projections 117 and 134 has a diameter 139 greater than the inside width 120 of the radial groove 118. The stop element AE or the disk 119 cannot therefore be inadvertently plugged onto the longitudinal portion 138 extending away from the projection 117 in the proximal direction.

A further optional component part of the instrument set is a gripping tool 140, which serves for manipulation of a rod 8 and which can also be used independently of the above-described screw manipulator 2. The gripping tool 140 has a rod-shaped shaft 144, at the proximal end of which there is a grip element serving to secure a rod 8, and at the other end of which an elongate handle 141 is arranged. The handle 141 is oriented such that its longitudinal direction 146 encloses, with the longitudinal direction 147 of the shaft 144, an angle α of less than 180° and more than 90°. This design is an ergonomic improvement compared to the gripping tools for this purpose in which the handle extends substantially coaxially with respect to the shaft 144. The gripping tool 140 permits a more comfortable position of the hand when inserting a rod into the recesses 13 of the pedicle screws 1 implanted in the spinal column. In particular, a pivoting movement of the shaft 114, for example in the direction of the double arrow 145 in FIG. 30, can be performed more easily and with the hand relaxed. Such pivoting of the shaft 144 is required, for example, when a curved rod 8 rather than a rectilinear one is intended to be inserted through a punctiform skin opening into the area of the spinal column that is to be stabilized. The angle between the handle 141 and the shaft 144 is preferably chosen such that the angle α lies in a range of 100° to 140°, more preferably in a range of 110° to 130°. In the illustrative embodiment shown in FIG. 30 et seq., there is an angle α of approximately 120°.

The shaft 144 and the handle 141 are each traversed in the longitudinal direction 146, 147 by a cavity 148, 149. The cavities are connected to each other at the connection point 150 of handle and shaft and accommodate an actuation mechanism 154, which is provided for bringing a grip element of the tool into a gripping position for clamping a rod 8 and into a release position for releasing the rod. The actuation mechanism 154 comprises a rod-shaped drive element 155, arranged axially movably in the cavity 148 of the handle 141, and a rod-shaped driven element 156 arranged axially movably in the cavity 149 of the shaft 144. At the connection point 150, the ends of said elements facing toward each other form a wedge mechanism. It is particularly advantageous that, apart from the drive element 155 and the driven element 156, no further component parts are needed by which a longitudinal axial movement of the drive element 155, needed to transfer the grip element to its gripping or releasing position, is converted to a longitudinal axial movement of the driven element 156. To allow force to be transferred in the most effective way possible, it is expedient if a beveled surface 157 present on the drive element 155 or on the driven element 156 is oriented such that it encloses, with the longitudinal direction 146, 147 of the drive element or of the driven element, respectively, an angle β which with a deviation of 20° corresponds to half the angle α enclosed by the longitudinal directions 146, 147. The value of the angle β is therefore in a range of 50° to 70°.

In the illustrative embodiment shown, a bore 158 passes through the driven element 156, the wall of which bore forms a first and a second beveled surface 157a, 157b (FIG. 38). To ensure that the orientation of the bore 158 and of the beveled surfaces 157 does not change, the driven element 156 is mounted in the cavity 149 in a manner fixed in rotation. The first beveled surface 157a points approximately in the distal direction and is acted upon by the drive element 155 when the latter is moved in the direction to the shaft 144 (arrow 159 in FIG. 40). The driven element 156 is thereby moved to the free end of the shaft 144, as is indicated by the arrow 60 in FIG. 40. The second beveled surface 157b, which points approximately in the proximal direction and has the same orientation as the first beveled surface 157a, is acted upon by the drive element 155 when the latter is moved in the reverse direction (counter to arrow 159). As a result of this, the driven element 156 is moved in the direction of the connection point 150 (counter to arrow 160). With the movement of the driven element in one direction or another, a grip element can be controlled, i.e. can be moved to its gripping or releasing position, as is explained in more detail below for the present illustrative embodiment.

The bore 158 preferably has a circular bore cross section. This design affords the possibility of using a drive element 155 which is mounted rotatably and axially displaceably in the handle, such that the advance in the direction of the arrow 159 and the retreat counter to the arrow 159 are effected by a screw drive, or the drive element 155 can be designed as a screw. It is advantageous here for the end of the drive element 155 cooperating with the beveled surface 157a, 157b, or in kinematic reversal for the end of the driven element 156, to be designed as a ball 164. In the illustrative embodiment shown, the end of the drive element 155 carrying the ball 164 protrudes into the bore 158. The diameter of the ball 164 is dimensioned such that it is guided in the bore 158 in a manner free of play or with slight radial play. In view of the angled arrangement of drive element and driven element, and in order to prevent a situation where the end of the drive element 155 extending into the bore 158 collides with the bore edge facing toward the handle 141, the bore edge has a recess 165 in a distal area. Moreover, the ball 164 is connected by a radially narrowed neck 166 to the rest of the longitudinal portion of the drive element 155.

The drive element 155 is designed as a screw, in other words has an outer thread 177 which cooperates with an inner thread 180 arranged on the inside wall of the cavity 148. Moreover, the drive element 155 protrudes with an overshoot 178 from the end of the handle 141 facing away from the shaft 144, and a handwheel 179 serving for the rotational actuation of the drive element 155 is arranged on the overshoot 178.

The end of the driven element 156 extending into the area of the connection point 150, and traversed by the bore 158, is radially widened and merges into a radially narrowed longitudinal portion via a shoulder 184 that tapers conically in the proximal direction. In the area of the connection point 150, the cavity 149 is designed complementing the above-described end of the driven element 156, i.e. it has a shoulder 185 facing in the distal direction and widening conically in this direction, which shoulder 185 forms an abutment for the shoulder 184 and limits the movement of the driven element 156 in the proximal direction, or in the direction of the arrow 160.

In the present illustrative embodiment, the abovementioned grip element is formed by the proximal end face 186 of the driven element 156. A bore 187, serving to receive the rod 8 and connected to the cavity 149, passes through the free end of the shaft 144. The central longitudinal axis 195 of the bore 188 runs in the plane spanned by the longitudinal directions 146, 147 of the handle 141 and of the shaft 144. In the gripping position (FIGS. 34 to 36), the grip element or the end face 186 presses the rod 8 against an area of the bore wall facing in the distal direction. In the release position, the end face 186 is arranged at an axial distance from the rod 8 (FIGS. 31 to 33), such that the rod 8 can be inserted into the bore 187 or removed therefrom. The end face 186 has a concave shape and is part of a cylinder surface having a surface curvature matching the curvature of the rod 8. In this way, the rod 8 is held in the bore 187 with a form fit. In order to rotationally fix the rod 8 in the bore 187, at least one projection 188 protrudes from the proximal end face 186. In order to fix the rod 8 in rotation, it has a recess which complements the at least one projection 188 and in which the projection 188 can engage. In the present illustrative embodiment, two rib-shaped projections 188 extending in the direction of the bore axis 189 are present on the end face 186. An end of a rod 8 received by the bore 187 preferably has a large number of recesses 190, which are designed complementing the rib-shaped projections 188. They extend in the direction of the central longitudinal axis 194 of the rod end inserted into the bore 187 and are distributed uniformly in the circumferential direction of the rod. The recesses form a structure like a toothed wheel on the rod 8. By virtue of this design of the rod 8, the latter can be inserted into the bore 187 in any desired rotation position and can be held rotationally fixed therein.

The invention claimed is:

1. An instrument set for percutaneous stabilization of a spinal column using rods and pedicle screws, the instrument set comprising:
   pedicle screws having a screw head and a screw shank and a distally open recess for receiving a rod;
   a screw manipulator formed with a central cavity passing axially therethrough and having a cylindrical sleeve and a slide;
   said cylindrical sleeve having a wall divided into two first wall segments by two diametrically opposite and axially extending windows that open out in a proximal end face of said sleeve;
   proximal ends of said first wall segments forming grip elements which, during a screw manipulation, receive between them at least a longitudinal portion of said screw head; and
   said slide being a hollow cylinder having a wall divided into two second wall segments by two diametrically opposite and axially extending windows opening out in a proximal end face of said hollow cylinder, said second wall segments being guided in an axially displaceable manner in said windows of said sleeve, and proximal end faces of said second wall segments each forming a holding-down element, one of said first wall segments or said second wall segments each having a respective axially extending rib protruding from a side edge thereof facing in a circumferential direction of said screw manipulator, and side edges of respective other wall segments of said first wall segments or said second wall segments each having a respective axially extending groove being formed therein, which said respective rib engages axially displaceably with a form fit effective in the circumferential direction;
   said slide being displaceable on said sleeve in the axial direction and being connected to and securing said first wall segments against moving radially apart at least in a proximal end position of displacement.

2. The instrument set according to claim 1, wherein said slide comprises at least one holding-down element at a proximal end thereof configured to, in the proximal end position of said slide, hold a rod inserted into a distally open recess of the screw head inside said recess.

3. The instrument set according to claim 2, wherein said at least one holding-down element, in the proximal end position of displacement of said slide, is at an axial distance from the end face of said sleeve, or of said first wall segments, that is smaller than an insertion depth by which said screw head protrudes axially into a receiving space limited laterally by said grip elements.

4. The instrument set according to claim 3, wherein the axial distance is less than or equal to a difference of the insertion depth and the thread length of an inner thread formed in said screw head and which serves to fix the rod with the aid of a fixing screw.

5. The instrument set according to claim 2, wherein said at least one holding-down element is arranged outside an imaginary cylinder which extends coaxially with respect to the central longitudinal axis of said sleeve and which has a diameter corresponding to a diameter of the outer thread of said fixing screw.

6. The instrument set according to claim 5, wherein said diameter of said imaginary cylinder corresponds to the external diameter of said screw head.

7. The instrument set according to claim 1, wherein the first wall segments extend over a greater arc length than the second wall segments.

8. The instrument set according to claim 1, wherein the outer surfaces of the first and second wall segments extend in a common cylindrical envelope surface.

9. The instrument set according to claim 1, wherein the distal ends of the first wall segments are connected to each other via a first cylinder portion and the distal ends of the second wall elements are connected to each other via a second cylinder portion, wherein an internal diameter of said first cylinder portion is greater than an external diameter of said second cylinder portion.

10. The instrument set according to claim 1, wherein an axial movement of said slide relative to said sleeve takes place via a helical gearing.

11. The instrument set according to claim 10, wherein an outer thread protrudes from the outer surface of the second wall segments and cooperates with an inner thread of an axially fixed adjusting nut that engages coaxially around said sleeve.

12. The instrument set according to claim 11, wherein, in order to axially fix said adjusting nut, a proximal and a distal abutment element protrude, at an axial distance from each other, from the outer surfaces of the first wall segments, which abutment elements enclose between them, and radially overlap, a counter-abutment element that protrudes radially inward from the inner surface of said adjusting nut.

13. The instrument set according to claim 12, wherein the distal abutment element is formed by the first cylinder portion, wherein the latter has a shoulder protruding radially beyond the outer surfaces of the first wall segments.

14. The instrument set according to claim 12, wherein the proximal abutment element is an abutment ring which engages around said sleeve and which is releasably connected to the first wall segments in an axially fixed manner.

15. The instrument set according to claim 12, wherein the counter-abutment element is the inner thread of said adjusting nut.

16. The instrument set according to claim 12, wherein said adjusting nut is arranged on the distal end of said sleeve.

17. The instrument set according to claim 16, wherein said adjusting nut engages around at least a longitudinal portion of said first cylinder portion.

18. The instrument set according to claim 1, comprising a rod-shaped screwdriver configured for insertion into the central cavity of said screw manipulator, and wherein a proximal end of said screwdriver carries a rotation actuation element that can be plugged into the recess of the screw head for joint rotation therewith.

19. The instrument set according to claim 18, comprising a stop mechanism with which the screwdriver inserted into the cavity can be stopped in an axial target position, in which position its rotation actuation element protrudes at least partially into the recess of the screw head.

20. The instrument set according to claim 19, wherein said stop mechanism comprises a projection protruding from the circumferential surface of the screwdriver, and a stop element which radially overlaps the distal side of said projection in the target position of the screwdriver and is axially fixed relative to said screw manipulator.

21. The instrument set according to claim 20, wherein said stop element is a separate stop element that is fixed releasably and in an axially fixed manner on the screw manipulator.

22. The instrument set according to claim 21, wherein said stop element is a disk formed with a radial groove, wherein an inside width of said radial groove is greater than the thickness or the diameter of a longitudinal portion of said screwdriver distally adjoining the projection, but smaller than a dimension of said projection in a direction extending transversely with respect to the central longitudinal axis of said screwdriver.

23. The instrument set according to claim 22, further comprising a locking connection, effective in the radial direction, between said disk and said screw manipulator.

24. The instrument set according to claim 23, wherein a resiliently mounted locking element protrudes from the proximal side of the disk and latches into an annular groove on the distal end face of said slide or of the second cylinder portion.

25. The instrument set according to claim 22, wherein an engage-behind element is arranged on the proximal side of said disk, which engage-behind element, in order to axially stop the screwdriver, can be plugged onto the screw manipulator in a joining direction extending transversely with respect to the central longitudinal axis of the screwdriver, thereby engaging behind a counter-element.

26. The instrument set according to claim 25, wherein the counter-element is the groove wall, facing toward the proximal end of the screw manipulator, of the annular groove present on the second cylinder portion.

27. The instrument set according to claim 25, wherein the engage-behind element is a flange extending in a U shape and arranged at an axial distance from the proximal side of the disk.

28. The instrument set according to claim 1, further comprising a gripping tool with a rod-shaped shaft, at the proximal end of which there is a grip element serving to secure a rod, and at the other end of which an elongate handle is arranged, wherein said handle is oriented such that its longitudinal direction encloses, with the longitudinal direction of the shaft, an angle $\alpha$ of less than 180° and more than 90°.

29. The instrument set according to claim 28, wherein the angle $\alpha$ lies between 100° and 140°.

30. The instrument set according to claim 29, wherein the angle $\alpha$ lies between 110° and 130°.

31. The instrument set according to claim 28, wherein said shaft and said handle are each traversed in the longitudinal direction by a cavity, the cavities being connected to each other at a connection point of said handle and said shaft, and wherein the cavities accommodate an actuation mechanism bringing said grip element into a gripping position for clamping said rod and into a release position for releasing said rod.

32. The instrument set according to claim 31, wherein said actuation mechanism comprises a rod-shaped drive element, arranged axially movably in the cavity of said handle, and a rod-shaped driven element arranged axially movably in the cavity of said shaft, wherein the ends of said drive element and of said driven element facing toward each other at the connection point form a wedge mechanism.

33. The instrument set according to claim 32, wherein a beveled surface present on said drive element or on said driven element is oriented such that it encloses, with the longitudinal direction of said drive element or driven element, respectively, an angle $\beta$ which with a deviation of 20° corresponds to half the angle $\alpha$ enclosed by the longitudinal directions.

34. The instrument set according to claim 32, wherein a bore passes through said drive element or said driven element, the wall of which bore forms at least one beveled surface, wherein the respective other element protrudes into the bore and cooperates with the at least one beveled surface in the manner of a wedge mechanism.

35. The instrument set according to claim 34, wherein the bore has a circular bore cross section, wherein said drive element or said driven element protrudes with a ball into the bore.

36. The instrument set according to claim 32, wherein said drive element has an outer thread cooperating with an inner thread of said handle, wherein said drive element protrudes from said handle with an overshoot, on which a handwheel is arranged.

37. The instrument set according to claim 32, wherein said grip element is formed by the proximal end face of said driven element.

38. The instrument set according to claim 37, wherein a bore, serving to receive said rod and connected to the cavity, passes through the free end of the shaft, wherein, in the gripping position, the grip element or the end face of the driven element presses the rod against an area of the bore wall facing in the distal direction.

39. The instrument set according to claim 38, wherein the proximal end face of the driven element has a concave shape and is part of a cylinder surface having a curvature complementing a surface curvature of said rod.

40. The instrument set according to claim 38, wherein, in order to fix said rod in rotation in the bore, at least one projection protrudes from the proximal end face of said driven element.

41. The instrument set according to claim 38, wherein the central longitudinal axis of the bore runs in a plane spanned by the longitudinal directions of said handle and of said shaft.

* * * * *